(12) United States Patent
Jeffs et al.

(10) Patent No.: US 12,274,684 B2
(45) Date of Patent: *Apr. 15, 2025

(54) TREATMENT OF VASCULOPATHY WITH PROSTACYCLIN AND MESENCHYMAL STEM CELLS

(71) Applicant: United Therapeutics Corporation, Silver Spring, MD (US)

(72) Inventors: Roger Jeffs, Chapel Hill, NC (US); Thomas Petersen, Durham, NC (US); Roger M. Ilagan, Burlington, NC (US); Michael Wade, Chapel Hill, NC (US)

(73) Assignee: United Therapeutics Corporation, Silver Spring, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/535,865

(22) Filed: Dec. 11, 2023

(65) Prior Publication Data

US 2024/0100003 A1    Mar. 28, 2024

Related U.S. Application Data

(60) Continuation of application No. 17/469,745, filed on Sep. 8, 2021, now Pat. No. 11,839,596, which is a division of application No. 16/137,629, filed on Sep. 21, 2018, now Pat. No. 11,141,393, which is a division of application No. 14/149,929, filed on Jan. 8, 2014, now Pat. No. 10,080,730.

(60) Provisional application No. 61/750,458, filed on Jan. 9, 2013.

(51) Int. Cl.
| | |
|---|---|
| *A61K 31/192* | (2006.01) |
| *A61K 31/557* | (2006.01) |
| *A61K 35/28* | (2015.01) |
| *C12N 5/0775* | (2010.01) |

(52) U.S. Cl.
CPC .......... *A61K 31/192* (2013.01); *A61K 31/557* (2013.01); *A61K 35/28* (2013.01); *C12N 5/0663* (2013.01); *C12N 2501/00* (2013.01); *C12N 2501/02* (2013.01)

(58) Field of Classification Search
None
See application file for complete search history.

(56) References Cited

U.S. PATENT DOCUMENTS

| | | | |
|---|---|---|---|
| 3,089,815 A | 5/1963 | Lieb et al. | |
| 4,352,883 A | 10/1982 | Lim | |
| 4,353,888 A | 10/1982 | Sefton | |
| 4,714,680 A | 12/1987 | Civin | |
| 4,965,204 A | 10/1990 | Civin | |
| 4,968,733 A | 11/1990 | Muller et al. | |
| 4,976,859 A | 12/1990 | Wechs | |
| 4,983,393 A | 1/1991 | Cohen et al. | |
| 5,026,365 A | 6/1991 | Rossini et al. | |
| 5,035,994 A | 7/1991 | Civin | |
| 5,071,741 A | 12/1991 | Brockbank | |
| 5,084,350 A | 1/1992 | Chang et al. | |
| 5,130,144 A | 7/1992 | Civin | |
| 5,137,809 A | 8/1992 | Loken et al. | |
| 5,158,881 A | 10/1992 | Aebischer et al. | |
| 5,284,761 A | 2/1994 | Aebischer et al. | |
| 5,643,192 A | 7/1997 | Hirsh et al. | |
| 5,651,982 A | 7/1997 | Marx | |
| 5,691,176 A | 11/1997 | Lebkowski et al. | |
| 5,693,531 A | 12/1997 | Chiorini et al. | |
| 5,750,397 A | 5/1998 | Tsukamoto et al. | |
| 5,800,828 A | 9/1998 | Dionne et al. | |
| 5,811,094 A | 9/1998 | Caplan et al. | |
| 6,387,369 B1 | 5/2002 | Pittenger et al. | |
| 6,468,527 B2 | 10/2002 | Austin et al. | |
| 7,638,128 B2 | 12/2009 | Dzau et al. | |
| 10,016,463 B2 | 7/2018 | Jeffs et al. | |
| 10,071,123 B2 | 9/2018 | Jeffs et al. | |
| 10,080,730 B2 * | 9/2018 | Jeffs | A61K 35/28 |
| 10,842,823 B2 | 11/2020 | Jeffs et al. | |
| 11,141,393 B2 * | 10/2021 | Jeffs | A61P 43/00 |
| 11,839,596 B2 * | 12/2023 | Jeffs | A61P 9/10 |
| 2003/0118567 A1 | 6/2003 | Stewart | |
| 2005/0165111 A1 | 7/2005 | Wade et al. | |
| 2007/0065414 A1 | 3/2007 | Freyman et al. | |
| 2008/0050349 A1 | 2/2008 | Stewart | |
| 2008/0226595 A1 | 9/2008 | Edinger et al. | |
| 2009/0177262 A1 | 7/2009 | Oberti et al. | |

(Continued)

FOREIGN PATENT DOCUMENTS

| | | |
|---|---|---|
| WO | WO-92/04033 A1 | 3/1992 |
| WO | WO-92/19195 A1 | 11/1992 |

(Continued)

OTHER PUBLICATIONS

"Second European Consensus Document on Chronic Critical Leg Ischemia", Circulation, Nov. 1991, 84(4 Suppl.):IV-1-IV-26.
Abisambra et al., "Abstracts for the 19th Annual Meeting of the American Society for Neural Therapy and Repair," Cell Transplantation, 2012, 21, pp. 773-797.
Actelion Pharmaceuticals, "VELETRI: epoprostenol," (2011); col. 1, para 5; col. 2, para 2.
Aizman et al., "Extracellular Matrix Produced by Bone Marrow Stromal Cells and by Their Derivative, SB623 Cells. Supports Neural Cell Growth," Journal of Neuroscience Research, 2009, 87, pp. 3198-3206.
Allen et al., "Type I collagen, fibrin and PuraMatrix matrices provide permissive environments for human endothelial and mesenchymal progenitor cells to form neovascular networks," Journal of Tissue Engineering and Regenerative Medicine, 2011, 5, pp. e74-e86.

(Continued)

*Primary Examiner* — Blaine Lankford
(74) *Attorney, Agent, or Firm* — Foley & Lardner LLP

(57) ABSTRACT

Provided are methods for treating or preventing vasculopathy in a subject in need thereof, comprising administering to the subject a prostacyclin and a mesenchymal stem cell (MSC) or a MSC-conditioned culture medium or administering to the subject a MSC or a MSC-conditioned culture medium that has treated with prostacyclin. Pharmaceutical compositions suitable for such treatments are also provided.

14 Claims, 11 Drawing Sheets

(56) References Cited

U.S. PATENT DOCUMENTS

| | | |
|---|---|---|
| 2009/0274665 A1 | 11/2009 | Akabutu et al. |
| 2010/0040584 A1 | 2/2010 | Melero-Martin et al. |
| 2011/0003008 A1 | 1/2011 | Lim |
| 2012/0172970 A1 | 7/2012 | Cottone et al. |
| 2014/0193379 A1 | 7/2014 | Jeffs et al. |
| 2014/0234278 A1 | 8/2014 | Heffner et al. |
| 2015/0216909 A1 | 8/2015 | Jeffs et al. |
| 2015/0246078 A1 | 9/2015 | Jeffs et al. |
| 2018/0110807 A1 | 4/2018 | Ilagan et al. |
| 2018/0280445 A1 | 10/2018 | Jeffs et al. |
| 2019/0008904 A1 | 1/2019 | Jeffs et al. |

FOREIGN PATENT DOCUMENTS

| | | |
|---|---|---|
| WO | WO-93/14191 A1 | 7/1993 |
| WO | WO-94/29438 A1 | 12/1994 |
| WO | WO-95/05452 A1 | 2/1995 |
| WO | WO-95/07611 A1 | 3/1995 |
| WO | WO-95/27071 A1 | 10/1995 |
| WO | WO-96/27287 A1 | 9/1996 |
| WO | WO-96/29862 A1 | 10/1996 |
| WO | WO-97/21824 A1 | 6/1997 |
| WO | WO-97/21825 A1 | 6/1997 |
| WO | WO-98/14058 A1 | 4/1998 |
| WO | WO-98/20027 A2 | 5/1998 |
| WO | WO-00/24897 A1 | 5/2000 |
| WO | WO-01/04268 A1 | 1/2001 |
| WO | WO-2004/050180 A2 | 6/2004 |
| WO | WO-2004/084921 A1 | 10/2004 |
| WO | WO-2004/085630 A1 | 10/2004 |
| WO | WO-2006/032092 A1 | 3/2006 |
| WO | WO-2009/057313 A1 | 5/2009 |
| WO | WO-2009/105044 A1 | 8/2009 |
| WO | WO-2012/027740 A1 | 3/2012 |
| WO | WO-2014/022373 A1 | 2/2014 |
| WO | WO-2014/022376 A2 | 2/2014 |

OTHER PUBLICATIONS

Asahara et al., "Isolation of Putative Progenitor Endothelial Cells for Angiogenesis," Science, Feb. 14, 1997, vol. 275, pp. 964-967.
Assmus et al., "Transplantation of Progenitor Cells and Regeneration Enhancement in Acute Myocardial Infarction (TOPCARE-AMI)," Circulation, Nov. 11, 2002, 106, pp. 3009-3017.
Barst, Robyn MD, FACC, "Is it Possible to Reverse the Endothelial Dysfunction in Pulmonary Arterial Hypertension?," Journal of the American College of Cardiology, 2007, 49(14), pp. 1572-1574.
Boeing et al., "Single-step isolation of extracellular vesicles by size-exclusion chromatography," Journal of Extracellular Vesicles, Sep. 8, 2014, 3:1:23430.
Bregni et al., "Human Peripheral Blood Hematopoietic Progenitors Are Optimal Targets of Retroviral-Mediated Gene Transfer," Blood, Sep. 15, 1992, 80(6), pp. 1418-1422.
Chen et al., "Effect on Left Ventricular Function of Intracoronary Transplantation of Autologous Bone Marrow Mesenchymal Stem Cell in Patients With Acute Myocardial Infarction," American Journal Cardiology, Jul. 2004, vol. 94, pp. 92-95.
Clinical All-Round, Nov. 2009, 58(11):2324-2337, with English-language translation of relevant part.
Coffin et al., "Development and Applications of Retroviral Vectors," Eds. Retroviruses, Cold Springs Harbor Laboratory Press, 1997, Chapter 9, pp. 437-473.
D'Alonzo et al., "Survival in Patients with Primary Pulmonary Hypertension," Ann. Intern. Med., Sep. 1, 1991, 115(5), pp. 343-349.
Das et al., "The Role of Hypoxia in Bone Marrow-Derived Mesenchymal Stem Cells: Considerations for Regenerative Medicine Approaches," Tissue Engineering: Part B, Apr. 1, 2010, 16(2), pp. 159-168.
Di Stefano et al., "The prostacyclin analogue iloprost increases circulating endothelial progenitor cells in patients with critical limb ischemia," Thrombosis and Haemostasis, Oct. 13, 2008, 100(5), pp. 871-877.
Dominici et al., "Minimal criteria for defining multipotent mesenchymal stromal cells. The International Society of Cellular Therapy position statement," Cytotherapy, 2006, 8(4), pp. 315-317.
Dormany et al., "Chronic Critical limb Ischemia," J. Vasc. Surg. 2000, 31, pp. S168-S175.
Doyle et al., "Endothelial Progenitor Cells," Endothelium, 2006, 13, pp. 403-410.
Eells et al., "Advances in Prostacyclin Therapy for Pulmonary Arterial Hypertension," Critical Care Nurse, Apr. 2004, 24(2), pp. 42-54.
Eneroth et al., "Amputation for occlusive arterial disease, A prospective multicentre study of 177 amputees," Int. Orthop. (SICOT), 1992, 16, pp. 383-387.
Flamme et al., "Induction of vasculogenesis and hematopoiesis in vitro," Development, 1992, 116(2), pp. 435-439.
Grant et al., "Iloprost: A Review of its Pharmacodynamic and Pharmacokinetic Properties, and Therapeutic Potential in Peripheral Vascular Disease, Myocardial Ischaemia and Extracorporeal Circulation Procedures," Drugs, 1992, 43(6}, pp. 889-924.
Groth et al., "Inflammatory cytokines in pulmonary hypertension," Respiratory Research, 2014, 15:47, 10 pages.
Gruber, Scott A., "The Case for Local Immunosuppression," Transplantation, Jul. 1992, 54, pp. 1-11.
Hall et al., "Endothelin receptor expression in idiopathic pulmonary arterial hypertension: effect of bosentan and epoprostenol treatment", European Respiratory Journal, vol. 38, No. 4, Mar. 15, 2011 (Mar. 15, 2011), pp. 851-860.
Hatzopoulos et al., "Isolation and characterization of endothelial progenitor cells from mouse embryos," Development, 1998, 125(8), pp. 1457-1468.
He et al., "Angiogenic Function of Prostacyclin Biosynthesis in Human Endothelial Progenitor Cells," Circulation Research, Jul. 3, 2008, vol. 103, No. 1, pp. 80-88.
Hill et al, "Circulating Endothelial Progenitor Cells, Vascular Function, and Cardiovascular Risk," N. Engl. J. Med., 2003, 348, pp. 593-600.
Hoogduijn et al., "The immunomodulatory properties of mesenchymal stem cells and their use for immunotherapy," International Immunopharmacology, 2010, 10, pp. 1496-1500.
Hu et al., "Exosomal miRNAs: biological properties and therapeutic potential," Frontiers in Genetics, Apr. 20, 2012, 3(56), pp. 1-9.
Humbert et al., "Cellular and Molecular Pathobiology of Pulmonary Arterial Hypertension," J. Am. Coll. Cardiol., 2004, 43(12:SuppIS), pp. 13S-24S.
Ingram et al., "Identification of a novel hierarchy of endothelial progenitor cells using human peripheral and umbilical cord blood," Blood, Jun. 29, 2004, 104, pp. 2752-2760.
Ishii et al., "Mesenchymal stem cell-based gene therapy with prostacyclin synthase enhanced neovascularization in hindlimb ischemia," Atherosclerosis, (2009) vol. 206, pp. 109-118.
Isner et al., "Angiogenesis and vasculogenesis as therapeutic strategies for postnatal neovascularization," J. Clin. Invest., May 1999, 103(9), pp. 1231-1236.
Kalka et al., "Transplantation of ex vivo expanded endothelial progenitor cells for therapeutic neovascularization," P.N.A.S., Mar. 29, 2000, 97(7), pp. 3422-3427.
Kamio et al., "Prostacyclin analogs stimulate VEGF production from human lung fibroblasts in culture," Am. J. Physiol. Lung Cell. Mol. Physiol., 2008, 294, pp. L1226-L1232.
Kamio et al., "Prostacyclin analogs stimulate VEGF production from human lung fibroblasts in culture", Am J Physiol Lung Cell Mol Physiol, vol. 294, pp. L1226-L1232 (2008).
Karlsson et al., "Nucleation and Growth of Ice Crystals Inside Cultured Hepatocytes During Freezing in the Presence of Dimethyl Sulfoxide," Biophysical J., Dec. 1993, 65, pp. 2524-2536.
Kawabe et al., "Role of Autocrine Prostacyclin System in Crucial Functions of Endothelial Progenitor Cells," Circ. J., 2008, 72 (Suppl. 1):503, PE-570.
Kawabe, "Q&A about Thrombosis (Part 6): Please explain prostacyclin and revascularization," Thrombosis and Circulation, 2011, 19(1):189-191.

(56) References Cited

OTHER PUBLICATIONS

Keeley et al., "Fibrocytes: Bringing new insights into mechanisms of inflammation and fibrosis," Int. J. Biochem. Cell Biol., 2010, 42, pp. 535-542.

Keily et al., "Pulmonary hypertension: diagnosis and management," BMJ, 2013, 346:f2028, 1-12.

Kuo et al., "Effect of Prostaglandin 12 Analogs on Cytokine Expression in Human Myeloid Dendritic Cells via Epigenetic Regulation," Molecular Medicine, 2012, 18, pp. 433-444.

Lai et al., "Exosome secreted by MSC reduces myocardial ischemia/reperfusion injury," Stem Cell Research, 2010, 4(3):214-222.

Lai et al., "Mesenchymal stem cell exosome: a novel stem cell-based therapy for cardiovascular disease," Regen. Med., 2011, 6(4):481-492.

Lau et al., "Stem Cells and Regenerative Medicine in Lung Biology and Diseases," Molecular Therapy, GB, (Mar. 6, 2012), Jun. 2012, vol. 20, No. 6, pp. 1116-1130.

Lee et al., "Exosomes Mediate the Cytoprotective A-ction of Mesenchymal Stromal Cells on Hypoxia-Induced Pulmonary Hypertension," Circulation, Oct. 31, 2012, 126(22), pp. 2601-2611.

Liu et al., "Engineered Endothelial Progenitor Cells That Overexpress Prostacyclin Protect Vascular Cells," Journal of Cellular Physiology, Mar. 20, 2012, 227(7), pp. 2907-2916.

Mayer et al., "Vascular endothelial growth factor (VEGF-A) expression in human mesenchymal stem cells: Autocrine and paracrine role on osteoblastic and endothelial differentiation," Journal of Cellular Biochemistry, vol. 95, No. 4, Jul. 1, 2005 (Jul. 1, 2005), pp. 827-839.

Murohara et al., "Transplanted cord blood-derived endothelial precursor cells augment postnatal neovascularization," J. Clin. Invest, Jun. 2000, 105(11), pp. 1527-1536.

Nagaya et al., "Hybrid Cell-Gene Therapy for Pulmonary Hypertension Based on Phagocytosing Action of Endothelial Progenitor Cells," Circulation, Jun. 30, 2003, 108, pp. 889-895.

Ribatti, Domenico, "The discovery of endothelial progenitor cells, An historical review," Leukemia Research, 2007, 31, pp. 439-444.

Risau et al., "Vasculogenesis and angiogenesis in embryonic-stem-cell-derived embryoid bodies," Development, 1988, 102, pp. 471-478.

Risau, Werner, "Differentiation of endothelium," FASEB J., 1995, 9(10), pp. 926-933.

Risau, Werner, "Mechanisms of angiogenesis," Nature, Apr. 17, 1997, 386, pp. 671-674.

Rissanen et al., "Gene therapy for therapeutic angiogenesis in critically ischaemic lower limb—on the way to the clinic," European Journal of Clinical Investigation, 2001, 31, pp. 651-666.

Ruan et al., "Prostacyclin therapy for pulmonary arterial hypertension," Texas Heart Institute Journal (2010) vol. 37, No. 4, pp. 391-399.

Sahara, Makoto, Clinic All-Round, 2009, 58(11), pp. 2324-2336, with English translation of indicated relevant portions.

Shantsila et al., "Endothelial Progenitor Cells in Cardiovascular Disorders," Journal of the American College of Cardiology vol. 49 (2007) p. 741-752; abstract; p. 745, col. 2 para 2-3.

Shintani, Satoshi, Heart View, 2011, 15(8): pp. 90-96, with English translation of indicated relevant portions.

Smadja et al., "Treprostinil increases the No. and angiogenic potential of endothelial progenitor cells in children with pulmonary hypertension," Angiogenesis, 2011, 14(1), pp. 17-27.

Smithies et al., "Insertion of DNA sequences into the human chromosomal Beta-globin locus by homologous recombination," Nature, Sep. 19, 1985, 317, pp. 230-234.

Takahashi et al., "Ischemia and cytokine induce-dmobilization of bone marrow derived endothelial progenitor cells for neovascularization," Nature Medicine, Apr. 1999, 5(4), pp. 434-438.

Thery et al., "Isolation and Characterization of Exosomes from Cell Culture Supernatants and Biological Fluids," Current Protocols in Cell Biol., 2006, 3.22.1-3.22.29.

Topol et al., "Combined Tissue-Type Plasminogen Activator and Prostacyclin Therapy for Acute Myocardial Infarction," J Am Coll Cardiol, 1989, 14(4), pp. 877-884.

Tyrrell et al., "Critical leg ischaemia: an appraisal of clinical definitions," Br. J. Surg., Feb. 1993, 80, pp. 177-180.

Umar et al., "Novel Approaches to Treat Experimental Pulmonary Arterial Hypertension: A Review," Journal of Biomedicine and Biotechnology, vol. 2010, pp. 1-11.

Wang et al., "Transplantation of Autologous Endothelial Progenitor Cells May Be Beneficial in Patients With Idiopathic Pulmonary Arterial Hypertension," J. Am. Coll. Cardiol., 2007, 49(14), pp. 1566-1571.

Williams et al., "Mesenchymal Stem Cells: Biology, Pathophysiology, Translational Findings, and Therapeutic Implications for Cardiac Disease," Circ Res. 2011;109:923-940; abstract; p. 925, col. 2, para 4.

Yoder et al., "Redefining endothelial progenitor cells via clonal analysis and hematopoietic stem/progenitor cell principals," Blood, 2007, 109, pp. 1801-1809.

Zhao et al., "Rescue of Monocrotaline-Induced Pulmonary Arterial Hypertension Using Bone Marrow-Derived Endothelial-Like Progenitor Cells," Circ. Res., 2006, 96, pp. 442-450.

Zhen et al., "Mesenchymal stem cell transplantation increases expression of vascular endothelial growth factor in papain-induced emphysematous lungs and inhibits apoptosis of lung cells," Cytotherapy, Sep. 1, 2010, 12(5), pp. 605-614.

Zheng et al., "Fidelity of targeted recombination in human fibroblasts and murine embryonic stem cells," Proc. Natl. Acad. Sci. USA, Sep. 1991, 88, pp. 8067-8071.

\* cited by examiner

TREATMENT OF VASCULOPATHY WITH PROSTACYCLIN AND MESENCHYMAL STEM CELLS

CROSS-REFERENCE TO RELATED APPLICATIONS

This application is a Continuation of U.S. application Ser. No. 17/469,745, filed Sep. 8, 2021, which is a Divisional of U.S. application Ser. No. 16/137,629, filed Sep. 21, 2018, which is a Divisional of U.S. application Ser. No. 14/149,929, filed Jan. 8, 2014, which claims the benefit under 35 U.S.C. § 119(e) to U.S. Provisional Application Ser. No. 61/750,458, filed Jan. 9, 2013, the contents of which are incorporated by reference in their entirety into the present disclosure.

BACKGROUND

The present application relates to the use of mesenchymal stem cells in treatment of vasculopathy, including pulmonary arterial hypertension (PAH) and other types of pulmonary hypertension, peripheral vascular disease (PVD), critical limb ischemia (CLI), coronary artery disease, diabetic vasculopathy, etc.

Pulmonary arterial hypertension is a progressive lung disorder which, untreated, leads to death on average within 2.8 years after being diagnosed. An increasing constriction of the pulmonary circulation leads to increased stress on the right heart, which may develop into right heart failure. By definition, the mean pulmonary arterial pressure (mPAP) in a case of chronic pulmonary hypertension is >25 mmHg at rest or >30 mmHg during exertion (normal value <20 mmHg). The pathophysiology of pulmonary arterial hypertension is characterized by vasoconstriction and remodeling of the pulmonary vessels. In chronic PAH there is neomuscularization of initially unmuscularized pulmonary vessels, and the vascular muscles of the already muscularized vessels increase in circumference. This increasing obliteration of the pulmonary circulation results in progressive stress on the right heart, which leads to a reduced output from the right heart and eventually ends in right heart failure (M. Humbert et al., J. Am. Coll. Cardiol. 2004, 43, 13 S-24S). PAH is an extremely rare disorder, with a prevalence of 1-2 per million. The average age of the patients has been estimated to be 36 years, and only 10% of the patients were over 60 years of age. Distinctly more women than men are affected (G. E. D'Alonzo et al., Ann. Intern. Med. 1991, 115, 343-349).

Standard therapies available on the market (e.g. prostacyclin analogues, endothelin receptor antagonists, phosphodiesterase inhibitors) are able to improve the quality of life, the exercise tolerance and the prognosis of the patients. The principles of these therapies are primarily hemodynamic, influencing vessel tone but having no direct influence on the pathogenic remodeling processes. In addition, the possibility of using these medicaments is restricted through the sometimes serious side effects and/or complicated types of administration. The period over which the clinical situation of the patients can be improved or stabilized by specific monotherapy is limited. Eventually the therapy escalates and thus a combination therapy is applied, where a plurality of medicaments must be given concurrently. Despite all the advances in the therapy of pulmonary arterial hypertension there is as yet no prospect of cure of this serious disorder.

The term peripheral vascular disease (PVD) refers to damage, dysfunction or obstruction within peripheral arteries and veins. Peripheral artery disease is the most common form of PVD. Peripheral vascular disease is the most common disease of the arteries and is a very common condition in the United States. It occurs mostly in people older than 50 years. Peripheral vascular disease is a leading cause of disability among people older than 50 years, as well as in those people with diabetes. About 10 million people in the United States have peripheral vascular disease, which translates to about 5% of people older than 50 years. The number of people with the condition is expected to grow as the population ages. Men are slightly more likely than women to have peripheral vascular disease.

Critical limb ischemia (CLI), due to advanced peripheral arterial occlusion, is characterized by reduced blood flow and oxygen delivery at rest, resulting in muscle pain at rest and non-healing skin ulcers or gangrene (Rissanen et al., Eur. J. Clin. Invest 31:651-666 (2001); Dormandy and Rutherford, J. Vasc. Surg. 31:S1-S296 (2000)). Critical limb ischemia is estimated to develop in 500 to 1000 per million individuals in one year ("Second European Consensus Document on Chronic Critical Leg Ischemia", Circulation 84 (4 Suppl.) IV 1-26 (1991)). In patients with critical limb ischemia, amputation, despite its associated morbidity, mortality and functional implications, is often recommended as a solution against disabling symptoms (M. R. Tyrrell et al., Br. J. Surg. 80: 177-180 (1993); M. Eneroth et al., Int. Orthop. 16: 383-387 (1992)). There exists no optimal medical therapy for critical limb ischemia (Circulation 84 (4 Suppl.): IV 1-26 (1991))

Coronary artery disease (atherosclerosis) is a progressive disease in humans wherein one or more coronary arteries gradually become occluded through the buildup of plaque. The coronary arteries of patients having this disease are often treated by balloon angioplasty or the insertion of stents to prop open the partially occluded arteries. Ultimately, these patients are required to undergo coronary artery bypass surgery at great expense and risk.

SUMMARY

In one embodiment, the current disclosure is directed to a method for treating or preventing vasculopathy in a subject in need thereof, comprising administering to the subject a prostacyclin and a composition comprising a mesenchymal stem cell (MSC) or a part of a culture medium that has been in contact with the MSC and contains one or more component(s) of the MSC. The prostacyclin and the composition can be administered concurrently or separately.

In some embodiments, prior to the administration, the MSC has been in contact with prostacyclin. Likewise, the culture medium or the MSC from which the culture medium is obtained can be placed in contact with prostacyclin, prior to such administration. Accordingly, in some embodiments, the method further includes such a pre-treatment step.

Non-limiting examples of components obtained from a part of the MSC culture include an exosome, a microvesicle, a microRNA, a messenger RNA, a non-coding RNA, a mitochondria, a growth factor, or combinations thereof.

Such methods, in one aspect, further entail administering to the subject an endothelial progenitor cell (EPC). In one aspect, the EPC is obtained from the subject. In some aspects, the EPC is transformed with a nucleic acid that increases the expression of biological activity of a protein selected from the group consisting of endothelial nitric oxide synthase (eNOS), heme oxygenase (HMOX1) and prostacyclin synthase (PTGIS). In one aspect, the nucleic acid encodes the protein.

Examples of prostacyclin include, without limitation, epoprostenol sodium, treprostinil, beraprost, ilprost, and a $PGI_2$ receptor agonist. In one aspect, the prostacyclin is treprostinil or a pharmaceutically acceptable salt or ester thereof.

Further provided, in embodiment, is a pharmaceutical composition comprising a therapeutically effective amount of a prostacyclin and a composition comprising a mesenchymal stem cell (MSC) or a culture medium that has been in contact with the MSC and contains compounds released from the MSC and a pharmaceutically acceptable carrier. In some aspects, the composition further comprises an endothelial progenitor cell (EPC).

Yet another embodiment provides a method for preparing a composition comprising a mesenchymal stem cell (MSC) or a culture medium that has been in contact with the MSC and contains compounds released from the MSC for in vivo delivery, comprising contacting the MSC with a prostacyclin. Treated composition obtainable by such a method is also provided.

In other embodiments, the pharmaceutical composition further comprises at least one pharmaceutically-acceptable carrier or at least one therapeutic agent. In another embodiment, the subject is suffering from vasculopathy, such as pulmonary arterial hypertension (PAH), peripheral vascular disease (PVD), critical limb ischemia (CLI), coronary artery disease, or diabetic vasculopathy. In other embodiments the current method reduces thrombosis in pulmonary arteries, reduces inflammation in pulmonary arteries, reduces the proliferation of intimal smooth muscle in pulmonary arteries, reduces the formation of plexiform lesions in pulmonary arteries, increases the amount of nitric oxide in pulmonary arteries, increases the amount of $PGI_2$ in pulmonary arteries, reduces the level of Endothelin-1 in pulmonary arteries, or reduces the amount of growth factors in pulmonary arteries. In other embodiments, the current method promotes proper endothelial morphology in pulmonary arteries.

BRIEF DESCRIPTION OF THE DRAWINGS

Provided as embodiments of this disclosure are drawings which illustrate by exemplification only, and not limitation.

Figure 1:
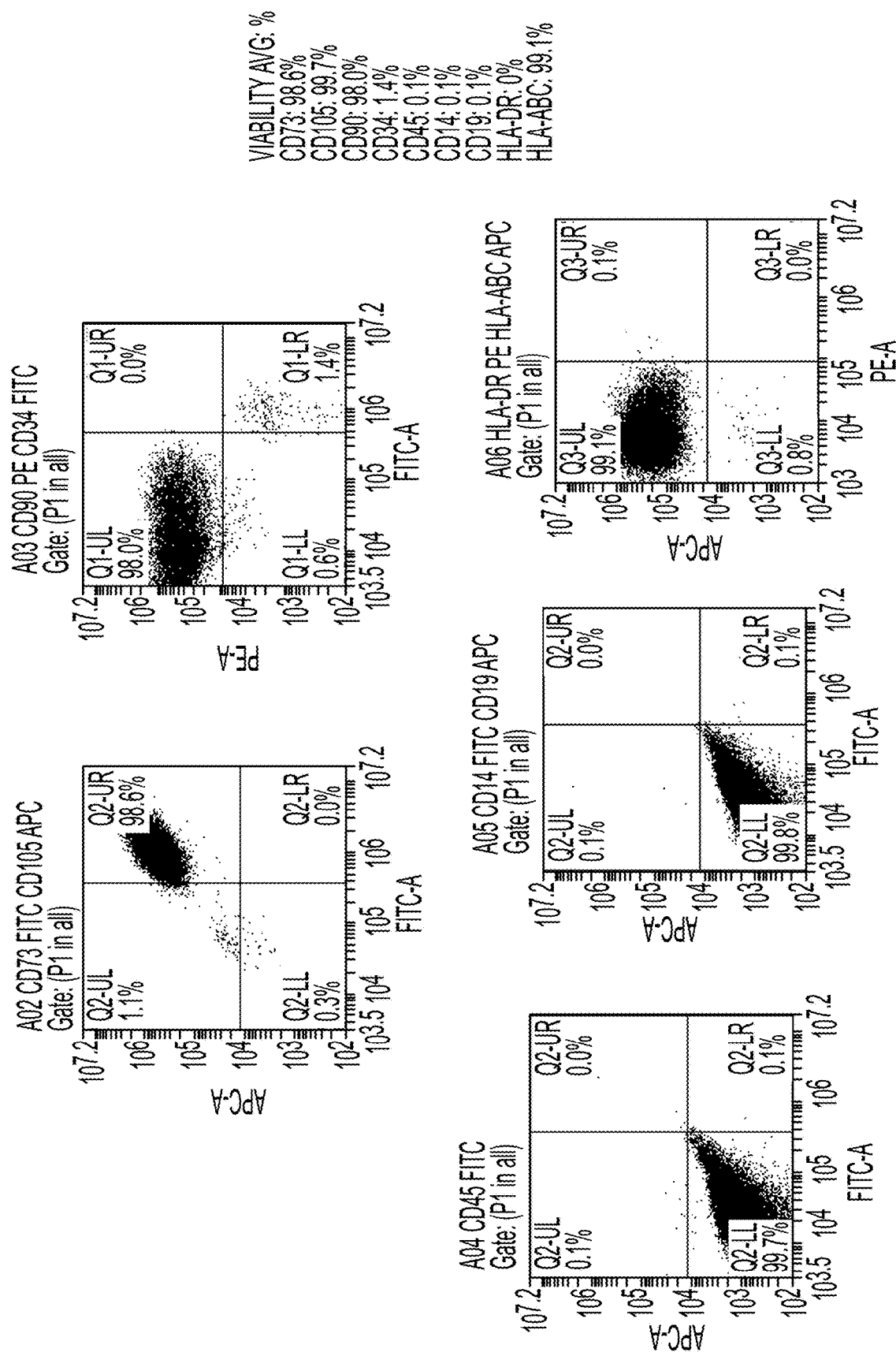
FIG. 1 shows the results of immunophenotype analysis of human bone marrow-derived MSC.

Some or all of the figures are schematic representations for exemplification; hence, they do not necessarily depict the actual relative sizes or locations of the elements shown. The figures are presented for the purpose of illustrating one or more embodiments with the explicit understanding that they will not be used to limit the scope or the meaning of the claims that follow below.

DETAILED DESCRIPTIONS

Unless otherwise specified, "a" or "an" means "one or more."

Unless specifically defined otherwise, all technical and scientific terms used herein shall be taken to have the same meaning as commonly understood by one of ordinary skill in the art (e.g., in stem cell biology, cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present), and are incorporated herein by reference.

It is herein discovered that both prostacyclin and mesenchymal stem cells (MSCs) possess therapeutic activities for vasculopathy. The combination of prostacyclin and MSCs, furthermore, produces synergistic effects. Such combination can be either co-administration, which can be concurrent or separate, of prostacyclin and MSCs to a patient, or administration to the patient a MSC composition that has been pre-treated with a prostacyclin.

It is shown that MSCs can ameliorate vasculopathy in patients, and it is contemplated that such a therapeutic effect is achieved due to MSCs' ability to improve the local microenvironment by delivering anti-inflammatory and pro-angiogenic factors to the diseased area. MSCs, however, are short-lived in the body and not regenerative.

Prostacyclin, such as treprostinil (TP), has been used for treating pulmonary arterial hypertension (PAH) patients. In this respect, prostacyclin has been shown to possess vasodilatory and anti-platelet aggregation activities.

An unexpected discovery is that prostacyclin can enhance the activity of MSCs for the treatment of vasculopathy, exhibiting synergism for such treatment. In this respect, it is observed that prostacyclin enhances MSCs' beneficial effect on blood vessel growth. For instance, prostacyclin increases the expression of VEGF at both protein and gene levels. Changes in secreted cytokines are also observed as a result of prostacyclin exposure. For instance, IL-6 is increased ~50-fold while MCP-1 is decreased ~6-7-fold.

Such synergism is also evident when the patient is further administered an endothelial progenitor cell (EPC). It is therefore contemplated that prostacyclin may enhance the activity of EPCs through MSCs. By virtue of such synergism, therefore, the combinatory use of prostacyclin and MSC, optionally together with EPC, can lead to improved therapeutic outcome and/or reduced need of each agent alone which, in turn, can result in reduced adverse effects potentially caused by each agent alone, at a higher dose.

It is further shown that such synergism is applicable to MSC-conditioned culture medium. To this end, it is observed that the exosomes of prostacyclin-treated MSC have higher levels of VEGF-A, which may promote increased VEGF production in target cells through a mechanism of horizontal gene transfer. Further, exposure to prostacyclin yields a more uniform population of exosomes.

As used herein, a "MSC-conditioned culture medium" refers to a culture medium that has been in contact with a MSC (e.g., for the purpose of culturing the MSC) and thus contains compounds released from the MSC. Non-limiting examples of such released compounds include exosomes or other microvesicles which can enclose messenger RNA, non-coding RNA, microRNAs, mitochondria, growth factors, or other types of bioactive agents.

A "culture medium" as used herein, encompasses (a) both a culture medium that contains the typical components used for culturing a MSC, such as amino acids, glucose, and various salts, with or without the MSC, and (b) a composition isolated from the culture medium that contains compounds released from the MSC during the culturing.

Accordingly, one embodiment of the present disclosure provides a method for treating or preventing vasculopathy in a subject in need thereof, comprising administering to the subject a prostacyclin and a composition comprising a mesenchymal stem cell (MSC) or a MSC-conditioned culture medium (collectively a "MSC composition").

In one aspect, the prostacyclin and the MSC composition are administered concurrently. In another aspect, the prostacyclin and the MSC composition are administered separately. When administered separately, the prostacyclin can be administered prior to, or following the administration of the MSC composition.

In another embodiment, provided is a method for treating or preventing vasculopathy in a subject in need thereof, comprising contacting a composition comprising an isolated mesenchymal stem cell (MSC) or a MSC-conditioned culture medium with a prostacyclin, and then administering the MSC composition to the subject.

Non-limiting examples of vasculopathy include pulmonary arterial hypertension (PAH), peripheral vascular disease (PVD), critical limb ischemia (CLI), coronary artery disease and diabetic vasculopathy.

As used herein, the term "subject" (also referred to herein as a "patient") includes warm-blooded animals, preferably mammals, including humans. In a preferred embodiment, the subject is a primate. In an even more preferred embodiment, the subject is a human.

As used herein the terms "treating", "treat" or "treatment" include administering a therapeutically effective amount of cells as defined herein sufficient to reduce or eliminate at least one symptom of vasculopathy.

As used herein the terms "preventing", "prevent" or "prevention" include administering a therapeutically effective amount of cells as defined herein sufficient to stop or hinder the development of at least one symptom of vasculopathy.

A. Prostacyclin

The term "prostacyclin" used herein explicitly comprises any prostaglandin 12 ($PGI_2$), any prostacyclin analogues, and any $PGI_2$ receptor agonists. Non-limiting examples of prostacyclin suitable for the present technology include epoprostenol sodium (e.g. Flolan®), treprostinil (e.g. TYVASO®, Remodulin®), ilprost (e.g. Ventavis®), and $PGI_2$ receptor agonist (e.g. Selexipag). In one aspect, the prostacyclin is treprostinil or a pharmaceutically acceptable salt or ester thereof.

B. Mesenchymal Stem Cells (MSCs)

Mesenchymal stem cells (MSCs) are cells found in bone marrow, blood, dental pulp cells, adipose tissue, skin, spleen, pancreas, brain, kidney, liver, heart, retina, brain, hair follicles, intestine, lung, lymph node, thymus, bone, ligament, tendon, skeletal muscle, dermis, and periosteum; and are capable of differentiating into different germ lines such as mesoderm, endoderm and ectoderm. Thus, MSCs are capable of differentiating into a large number of cell types including, but not limited to, adipose, osseous, cartilaginous, elastic, muscular, and fibrous connective tissues. The specific lineage-commitment and differentiation pathway which these cells enter depends upon various influences from mechanical influences and/or endogenous bioactive factors, such as growth factors, cytokines, and/or local microenvironmental conditions established by host tissues. MSCs are thus non-hematopoietic progenitor cells which divide to yield daughter cells that are either stem cells or are precursor cells which in time will irreversibly differentiate to yield a phenotypic cell. Examples of MSCs include mesenchymal precursor cells (MPCs).

As used herein, the term "stem cell" refers to self-renewing cells that are capable of giving rise to phenotypically and genotypically identical daughters as well as at least one other final cell type (e.g., terminally differentiated cells). The term "stem cells" includes totipotential, pluripotential and multipotential cells, as well as progenitor and/or precursor cells derived from the differentiation thereof.

As used herein, the term "totipotent cell" or "totipotential cell" refers to a cell that is able to form a complete embryo (e.g., a blastocyst).

As used herein, the term "pluripotent cell" or "pluripotential cell" refers to a cell that has complete differentiation versatility, i.e., the capacity to grow into any of the mammalian body's approximately 260 cell types. A pluripotent cell can be self-renewing, and can remain dormant or quiescent within a tissue.

The term "multipotential cell" or "multipotent cell" refers to a cell which is capable of giving rise to any of several mature cell types. As used herein, this phrase encompasses adult or embryonic stem cells and progenitor cells, and multipotential progeny of these cells. Unlike a pluripotent cell, a multipotent cell does not have the capacity to form all of the cell types.

As used herein, the term "progenitor cell" or "precursor cell" refers to a cell that is committed to differentiate into a specific type of cell or to form a specific type of tissue.

In a preferred embodiment, cells used in the methods of the disclosure are enriched from a sample obtained from a subject. The terms 'enriched', 'enrichment' or variations thereof are used herein to describe a population of cells in which the proportion of one particular cell type or the proportion of a number of particular cell types is increased when compared with the untreated population.

In a preferred embodiment, the cells used in the present disclosure are $TNAP^+$, $STRO-1^+$, $VCAM-1^+$, $THY-1^+$, $STRO-2^+$, $CD45^+$, $CD146^+$, $3G5^+$ or any combination thereof.

When we refer to a cell as being "positive" for a given marker it may be either a low (lo or dim) or a high (bright, bri) expresser of that marker depending on the degree to which the marker is present on the cell surface, where the terms relate to intensity of fluorescence or other color used in the color sorting process of the cells. The distinction of lo (or dim or dull) and bri will be understood in the context of the marker used on a particular cell population being sorted. When we refer herein to a cell as being "negative" for a given marker, it does not mean that the marker is not expressed at all by that cell. It means that the marker is expressed at a relatively very low level by that cell, and that it generates a very low signal when detectably labeled.

When used herein the term "TNAP" is intended to encompass all isoforms of tissue non-specific alkaline phosphatase. For example, the term encompasses the liver isoform (LAP), the bone isoform (BAP) and the kidney isoform (KAP). In a preferred embodiment, the TNAP is BAP. In a particularly preferred embodiment, TNAP as used herein refers to a molecule which can bind the STRO-3 antibody produced by the hybridoma cell line deposited with ATCC on 19 Dec. 2005 under the provisions of the Budapest Treaty under deposit accession number PTA-7282.

Stem cells useful for the methods can be derived from adult tissue, an embryo, extraembryonic tissue, or a fetus. The term "adult" is used in its broadest sense to include a postnatal subject. In a preferred embodiment, the term "adult" refers to a subject that is postpubertal. The term, "adult" as used herein can also include cord blood taken from a female.

In some aspects, the stem cells can be progeny cells (which can also be referred to as expanded cells) which are produced from the in vitro culture of the stem cells described herein. Expanded cells of the disclosure may have a wide variety of phenotypes depending on the culture conditions (including the number and/or type of stimulatory factors in the culture medium), the number of passages and the like. In certain embodiments, the progeny cells are obtained after about 2, about 3, about 4, about 5, about 6, about 7, about 8, about 9, or about 10 passages from the parental population. However, the progeny cells may be obtained after any number of passages from the parental population.

The progeny cells can be obtained by culturing in any suitable medium. The term "medium", as used in reference to a cell culture, includes the components of the environment surrounding the cells. Media may be solid, liquid, gaseous or a mixture of phases and materials. Media include liquid growth media as well as liquid media that do not sustain cell growth. Media also include gelatinous media such as agar, agarose, gelatin and collagen matrices. The term "medium" also refers to material that is intended for use in a cell culture, even if it has not yet been contacted with cells. In other words, a nutrient rich liquid prepared for bacterial culture is a medium.

In an embodiment, the progeny cells are obtained by isolating TNAP+ cells from bone marrow using magnetic beads labelled with the STRO-3 antibody, and plated in α-MEM supplemented with 20% fetal calf serum, 2 mM L-glutamine and 100 μm L-ascorbate-2-phosphate.

In one embodiment, such expanded cells (at least after 5 passages) can be TNAP−, CC9+, HLA class I+, HLA class II−, CD14−, CD19−; CD3−, CD11a−c−, CD31−, CD86− and/or CD80−. However, it is possible that under different culturing conditions to those described herein that the expression of different markers may vary. Also, whilst cells of these phenotypes may predominate in the expended cell population it does not mean that there is not a minor proportion of the cells that do not have this phenotype(s) (for example, a small percentage of the expanded cells may be CC9−). In one preferred embodiment, expanded cells of the disclosure still have the capacity to differentiate into different cell types.

In one embodiment, an expended cell population used in the methods of the disclosure comprises cells wherein at least 25%, more preferably at least 50%, of the cells are CC9+.

In another embodiment, an expended cell population used in the methods of the disclosure comprises cells wherein at least 40%, more preferably at least 45%, of the cells are STRO-1+.

In a further embodiment, the progeny cells may express markers selected from the group consisting of LFA-3, THY-1, VCAM-1, PECAM-1, P-selectin, L-selectin, 3G5, CD49a/CD49b/CD29, CD49c/CD29, CD49d/CD29, CD29, CD18, CD61, integrin beta, 6-19, thrombomodulin, CD10, CD13, SCF, PDGF-R, EGF-R, IGF1-R, NGF-R, FGF-R, Leptin-R, (STRO-2=Leptin-R), RANKL, STRO-1bright and CD146 or any combination of these markers.

In one embodiment, the progeny cells are Multipotential Expanded MSC Progeny (MEMPs) as defined in WO 2006/032092. Methods for preparing enriched populations of MSC from which progeny may be derived are described in WO 01/04268 and WO 2004/085630. In an in vitro context MSCs will rarely be present as an absolutely pure preparation and will generally be present with other cells that are tissue specific committed cells (TSCCs). WO 01/04268 refers to harvesting such cells from bone marrow at purity levels of about 0.1% to 90%. The population comprising MSC from which progeny are derived may be directly harvested from a tissue source, or alternatively it may be a population that has already been expanded ex vivo.

For example, the progeny may be obtained from a harvested, unexpanded, population of substantially purified MSC, comprising at least about 0.1, 1, 5, 10, 20, 30, 40, 50, 60, 70, 80 or 95% of total cells of the population in which they are present. This level may be achieved, for example, by selecting for cells that are positive for at least one marker selected from the group consisting of TNAP, STRO-1$^{bri}$, 3G5+, VCAM-1, THY-1, CD146 and STRO-2.

The MSC starting population may be derived from any one or more tissue types set out in WO 01/04268 or WO 2004/085630, namely bone marrow, dental pulp cells, adipose tissue and skin, or perhaps more broadly from adipose tissue, teeth, dental pulp, skin, liver, kidney, heart, retina, brain, hair follicles, intestine, lung, spleen, lymph node, thymus, pancreas, bone, ligament, bone marrow, tendon and skeletal muscle.

MEMPS can be distinguished from freshly harvested MSCs in that they are positive for the marker STRO-1bri and negative for the marker Alkaline phosphatase (ALP). In contrast, freshly isolated MSCs are positive for both STRO-1$^{bri}$ and ALP. In a preferred embodiment of the present disclosure, at least 15%, 20%, 30%, 40%, 50%, 60%, 70%, 80%, 90% or 95% of the administered cells have the phenotype STRO-1$^{bri}$, ALP−. In a further preferred embodiment the MEMPS are positive for one or more of the markers Ki67, CD44 and/or CD49c/CD29, VLA-3, α3β1. In yet a further preferred embodiment the MEMPs do not exhibit TERT activity and/or are negative for the marker CD18.

In one embodiment, the cells are taken from a patient with vasculopathy, cultured in vitro using standard techniques and administered to a patient as an autologous or allogeneic transplant. In an alternative embodiment, cells of one or more of the established human cell lines are used. In another useful embodiment of the disclosure, cells of a non-human animal (or if the patient is not a human, from another species) are used.

The present technology can be practiced using cells from any non-human animal species, including but not limited to non-human primate cells, ungulate, canine, feline, lagomorph, rodent, avian, and fish cells. Primate cells with which the disclosure may be performed include but are not limited to cells of chimpanzees, baboons, cynomolgus monkeys, and any other New or Old World monkeys. Ungulate cells with which the disclosure may be performed include but are not limited to cells of bovines, porcines, ovines, caprines, equines, buffalo and bison. Rodent cells with which the disclosure may be performed include but are not limited to mouse, rat, guinea pig, hamster and gerbil cells. Examples of lagomorph species with which the disclosure may be performed include domesticated rabbits, jack rabbits, hares, cottontails, snowshoe rabbits, and pikas. Chickens (*Gallus gallus*) are an example of an avian species with which the disclosure may be performed.

Cells can be stored before use. Methods and protocols for preserving and storing of eukaryotic cells, and in particular mammalian cells, are well known in the art (cf., for example, Pollard, J. W. and Walker, J. M. (1997) Basic Cell Culture Protocols, Second Edition, Humana Press, Totowa, N.J.; Freshney, R. I. (2000) Culture of Animal Cells, Fourth Edition, Wiley-Liss, Hoboken, N.J.). Any method maintaining the biological activity of the isolated stem cells such as mesenchymal stem/progenitor cells, or progeny thereof, may be utilized in connection with the present disclosure. In one preferred embodiment, the cells are maintained and stored by using cryo-preservation.

Cells can be obtained using a variety of techniques. For example, a number of cell-sorting techniques by which cells are physically separated by reference to a property associated with the cell-antibody complex, or a label attached to the antibody can be used. This label may be a magnetic particle or a fluorescent molecule. The antibodies may be cross-linked such that they form aggregates of multiple cells, which are separable by their density. Alternatively the antibodies may be attached to a stationary matrix, to which the desired cells adhere.

In a preferred embodiment, an antibody (or other binding agent) that binds TNAP+, STRO-1+, VCAM-1+, THY-1+, STRO-2+, 3G5+, CD45+, CD146+ is used to isolate the cells. More preferably, an antibody (or other binding agent) that binds TNAP+ or STRO-1+ is used to isolate the cells.

Various methods of separating antibody-bound cells from unbound cells are known. For example, the antibody bound to the cell (or an anti-isotype antibody) can be labelled and then the cells separated by a mechanical cell sorter that detects the presence of the label. Fluorescence-activated cell sorters are well known in the art. In one embodiment, anti-TNAP antibodies and/or an STRO-1 antibodies are attached to a solid support. Various solid supports are known to those of skill in the art, including, but not limited to, agarose beads, polystyrene beads, hollow fiber membranes, polymers, and plastic petri dishes. Cells that are bound by the antibody can be removed from the cell suspension by simply physically separating the solid support from the cell suspension.

Super paramagnetic microparticles may be used for cell separations. For example, the microparticles may be coated with anti-TNAP antibodies and/or STRO-1 antibodies. The antibody-tagged, super paramagnetic microparticles may then be incubated with a solution containing the cells of interest. The microparticles bind to the surfaces of the desired stem cells, and these cells can then be collected in a magnetic-field.

In another example, the cell sample is allowed to physically contact, for example, a solid phase-linked anti-TNAP monoclonal antibodies and/or anti-STRO-1 monoclonal antibodies. The solid-phase linking can comprise, for instance, adsorbing the antibodies to a plastic, nitrocellulose, or other surface. The antibodies can also be adsorbed on to the walls of the large pores (sufficiently large to permit flow-through of cells) of a hollow fiber membrane. Alternatively, the antibodies can be covalently linked to a surface or bead, such as Pharmacia Sepharose 6 MB macrobeads. The exact conditions and duration of incubation for the solid phase-linked antibodies with the stem cell containing suspension will depend upon several factors specific to the system employed. The selection of appropriate conditions, however, is well within the skill of the art.

The unbound cells are then eluted or washed away with physiologic buffer after allowing sufficient time for the stem cells to be bound. The unbound cells can be recovered and used for other purposes or discarded after appropriate testing has been done to ensure that the desired separation had been achieved. The bound cells are then separated from the solid phase by any appropriate method, depending mainly upon the nature of the solid phase and the antibody. For example, bound cells can be eluted from a plastic petri dish by vigorous agitation. Alternatively, bound cells can be eluted by enzymatically "nicking" or digesting an enzyme-sensitive "spacer" sequence between the solid phase and the antibody. Spacers bound to agarose beads are commercially available from, for example, Pharmacia.

The eluted, enriched fraction of cells may then be washed with a buffer by centrifugation and said enriched fraction may be cryopreserved in a viable state for later use according to conventional technology, culture expanded and/or introduced into the patient.

C. MSC-Conditioned Culture Media

It is discovered that MSCs can carry out their activities through compounds that can be released into the extracellular environment during growth or differentiation. In some aspects, such compounds include a microvesicle, referred to as exosome, which is between about 30 nm and about 200 nm in diameter. Exosomes can be internalized by host cells in vivo.

Exosomes are vesicles derived from the multivesicular body sorting pathway. Recent studies show that exosomes are bioactive vesicles useful for intercellular communication and facilitation of the immunoregulatory process. MSC exosomes contain 20S proteasomes and numerous RNAs (messenger RNA, non-coding RNA, microRNA).

In addition to exosomes, MSC also release other bioactive molecules/vesicles useful for the purpose of the present disclosure. Such molecules and vesicles include, without limitation, mitochondria and growth factors. Method of preparing culture media that contain such molecules and vesicles released from MSC and further isolating particular molecules and vesicles are known in the art. See, for instance, Hu et al., Frontiers in Genetics, 2:56, 1-9 (2012).

D. Pre-Treatment of MSC with Prostacyclin

In some embodiments, prior to coadministering a MSC or a MSC-conditioned culture medium with prostacyclin to a patient, the MSC or MSC-conditioned culture medium can be optionally pre-treated with prostacyclin. Accordingly, also provided, in one embodiment, is a method for preparing a mesenchymal stem cell (MSC) or MSC-conditioned culture medium for in vivo delivery, comprising contacting the MSC or MSC-conditioned culture medium with a prostacyclin. Yet another embodiment provides a treated MSC or MSC-conditioned culture medium obtainable by such a method.

Pre-treatment of a cell or a medium with a chemical compound encompasses known techniques. In one aspect, the prostacyclin can be added to and co-incubated with a culture medium that contains a MSC. Optionally, however, such co-incubation can further involve the addition of a growth factor (e.g., VEGF and Angiopoietin-1 or -2, platelet-derived growth factor) and/or hypoxia.

MSCs or MSC-conditioned culture media can be treated with prostacyclin in various ways. For example, prostacyclin can be used to treat MSCs ex vivo during the expansion of MSCs; prostacyclin can also be used to treat MSCs after administration. In some aspects, the concentration of prostacyclin is at least about 100 µg/mL, or at least about 150 µg/mL, 200 µg/mL, or 250 µg/mL. In some aspects, the concentration of prostacyclin is not more than about 400 µg/mL, or not more than about 350 µg/mL, 300 µg/mL or 250 µg/mL.

According to one embodiment of the present disclosure, MSCs can be prepared from the recipient's own blood or bone marrow. In that case, prostacyclin can also be used to treat MSCs before they are isolated from the recipients.

E. Endothelial progenitor cell (EPC)

As provided, the synergism between prostacyclin and MSCs for the treatment of vasculopathy is also evident when a patient is further administered with an endothelial progenitor cell (EPC). Thus, for any embodiment of the presently disclosed method, the patient further is administered an endothelial progenitor cell (EPC).

In some embodiments, the EPC can also be pre-treated with prostacyclin. The EPCs treated with prostacyclin exhibit a hyperproliferative phenotype with enhanced angiogenic properties, which are advantageous in treating vasculopathy compared to untreated EPCs.

EPCs can be treated with prostacyclin in various ways. For example, prostacyclin can be used to treat EPCs ex vivo during the expansion of EPCs; prostacyclin can be co-administered with EPCs to the recipient; prostacyclin can also be used to treat EPCs after transplantation. According to one embodiment of the present disclosure, EPCs are prepared from the recipient's own blood or bone marrow. In that case, prostacyclin can also be used to treat EPCs before they are isolated from the recipients.

An EPC is an undifferentiated cell that can be induced to proliferate. EPCs are capable of self-maintenance, such that with each cell division, at least one daughter cell will also be an EPC cell. EPCs are capable of being expanded 100, 250, 500, 1000, 2000, 3000, 4000, 5000 or more fold.

Phenotyping of EPCs reveals that these cells express the committed hematopoietic marker CD45. Additionally, an EPC may be immunoreactive for VEGFR-2 and/or Tie-2. Optionally, the EPC is immunoreactive for CD14. The EPC is a multipotent progenitor cell.

Vascular endothelial growth factor (VEGF) acts through specific tyrosine kinase receptors that includes VEGFR-1 (flt-1) and VEGFR-2 (flk-1/KDR) and VEGFR-3/Flt-4 which convey signals that are essential for embryonic angiogenesis and hematopoiesis. While VEGF binds to all three receptors, most biological functions are mediated via VEGFR-2 and the role of VEGFR-1 is currently unknown. VEGFR3/Flt4 signaling is known to be important for the development of lymphatic endothelial cells and VEGFR3 signaling may confer lymphatic endothelial-like phenotypes to endothelial cells. VEGFRs relay signals for processes essential in stimulation of vessel growth, vasorelaxation, induction of vascular permeability, endothelial cell migration, proliferation and survival. Endothelial cells express all different VEGF-Rs. During embryogenesis, it has been reported that a single progenitor cell, the hemangioblast can give rise to both the hematopoietic and vascular systems.

Tie-2 is an endothelial-specific receptor tyrosine kinase and a receptor for angiopoietin 1. It is a type I membrane protein that is expressed predominantly in the endothelium of actively growing blood vessels and may represent the earliest mammalian endothelial cell lineage marker. Tie-2 is likely involved in the regulation of endothelial cell proliferation and differentiation and may direct the special orientation of endothelial cells during the formation of blood vessels.

The CD14 antigen is a high affinity receptor for the complex of lipopolysaccharides (LPS) and LPS-Binding protein (LBP). The CD14 antigen is part of the functional heteromeric LPS receptor complex comprised of CD14, TLR4 and MD-2. CD14 is strongly expressed on most human monocytes and macrophages in peripheral blood, other body fluids and various tissues, such as lymph nodes and spleen. CD14 is weakly expressed on subpopulations of human neutrophils and myeloid dendritic cells.

The CD45 antigen is a tyrosine phosphatase, also known as the leukocyte common antigen (LCA). CD45 is present on all human cells of hematopoietic origin, except erythroid cells, platelets and their precursor cells. The CD45 molecule is required for T cell and B cell activation and is expressed in at least 5 isoforms, depending on the activation status of the cell.

VEGFR-1+, VEGFR-2+ and Tie-2+ cells constituted approximately 3.0.+−0.0.2%, 0.8.+−0.0.5%, 2.0.+−0.0.3% of the total population of mononuclear cells in blood respectively. CD14+/VEGFR-2+ cells constituted approximately 2.0.+−0.0.5% of the total population of monocytes and 0.08.+−0.0.04% of mononuclear cells in blood.

EPCs can be maintained in vitro in long-term cultures. The EPCs are capable of being passed in culture 2, 3, 4, 5, 6, 7, 8, 9, 10, 11, 12 or more times.

EPCs comprise endothelial colony-forming cells, typically developed after 1-3 weeks of cell culture. Endothelial colony-forming cells have the characteristics of precursor cells committed to the endothelial lineage and are capable of merging into neovessels, according to Smardj a et al., Angiogenesis 14(1):17-27 (2011).

The isolation, purification, ex vivo culturing and characterizing of EPCs are described in Hill et al, N. Engl. J. Med. 348:593-600 (2003), Assmus et al., Circulation 106:3009-16 (2002), Wang et al., J. Am. Coll. Cardiol. 49:1566-71 (2007), and Kalka et al., P.N.A.S. 97:3422-7 (2000), the content of which are hereby incorporated by reference in their entireties. Further, the isolation, purification, ex vivo culturing and characterizing of endothelial colony-forming cells are described in Yoder et al., Blood 109:1801-1809 (2007), Ingram et al., Blood 104:2752-2760 (2004), and Smardja et al., Angiogenesis 14(1):17-27 (2011), the content of which are hereby incorporated by reference in their entireties.

For example, the population of cells are isolated by means of positive selection, or by a mixture of both positive and negative selection in either order. The population of progenitor cells is purified. A purified population of EPCs contains a significantly higher proportion of EPCs than the crude population of cells from which the cells are isolated.

For example, the purification procedure should lead at least to a five-fold increase, preferably at least a ten-fold increase, more preferably at least a fifteen fold increase, most preferably at least a twenty fold increase, and optimally at least a twenty-five fold increase in EPCs with respect to the total population. The purified population of EPC should include at least 15%, preferably at least 20%, more preferably at least 25%, most preferably at least 35%, and optimally at least 50% of EPCs.

The methods described herein can lead to mixtures comprising up to 75%, preferably up to 80%, more preferably up to 85%, most preferably up to 90% and optimally up to 95% of stem cells. Such methods are capable of producing mixtures comprising 99%, 99.90% and even 100% of EPCs. Accordingly, the purified populations of the disclosure contain significantly higher levels of EPCs than those that exist in nature, as described above.

The purified population of EPCs can be isolated by contacting a crude mixture of cells containing a population of stem cells that express an antigen characteristic of the EPCs with a molecule that binds specifically to the extracellular portion of the antigen. Such a technique is known as positive selection. The binding of the EPCs to the molecule permit the EPCs to be sufficiently distinguished from contaminating cells that do not express the antigen to permit isolating the stem cells from the contaminating cells. The antigen is preferably VEGFR, and more preferably VEGFR-2.

The molecule used to separate progenitor cells from the contaminating cells can be any molecule that binds specifically to the antigen that characterizes the EPCs. The molecule can be, for example, a monoclonal antibody, a fragment of a monoclonal antibody, or, in the case of an antigen that is a receptor, the ligand of that receptor. For example, in the case of a VEGF receptor, such as FLK-1, the ligand is VEGF.

The unique isolated cells of the present disclosure can be separated from other cells by virtue of their CD45+ state and possession of vascular endothelial growth factor receptors (VEGFR), e.g. VEGFR-2. The cells can be isolated by conventional techniques for separating cells, such as those described in Civin, U.S. Pat. Nos. 4,714,680, 4,965,204, 5,035,994, and 5,130,144, Tsukamoto et al U.S. Pat. No. 5,750,397, and Loken et al, U.S. Pat. No. 5,137,809, each of which are hereby incorporated by reference in their entireties. Thus, for example, a CD45 specific monoclonal antibody or a VEGFR-specific antibody can be immobilized on a solid support such as nitrocellulose, agarose beads, polystyrene beads, hollow fiber membranes, magnetic beads, and plastic petri dishes. The entire cell population is then be passed through the solid support or added to the beads.

Cells that are bound to the binding molecule can be removed from the cell suspension by physically separating the solid support from the remaining cell suspension. For example, the unbound cells may be eluted or washed away with physiologic buffer after allowing sufficient time for the solid support to bind the stem cells.

The bound cells can be separated from the solid phase by any appropriate method, depending mainly upon the nature of the solid phase and the binding molecule. For example, bound cells can be eluted from a plastic petri dish by vigorous agitation. Alternatively, bound cells can be eluted by enzymatically "nicking" or digesting an enzyme-sensitive "spacer" sequence between the solid phase and an antibody. Suitable spacer sequences bound to agarose beads are commercially available from, for example, Pharmacia.

The eluted, enriched fraction of cells may then be washed with a buffer by centrifugation and preserved in a viable state at low temperatures for later use according to conventional technology. The cells may also be used immediately, for example by being infused intravenously into a recipient.

Those which remain attached to the solid support are those cells which contain a marker which is recognized by the antibody used. Thus, if the anti-CD45 antibody is used, then the resulting population will be greatly enriched in CD45+ cells. If the antibody used is VFGFR, then the resulting population will be greatly enriched in VEGFR+ cells. That population may then be enriched in the other marker by repeating the steps using a solid phase having attached thereto an antibody to the other marker.

Another way to sort CD45+ VEGFR+ cells is by means of flow cytometry, most preferably by means of a fluorescence-activated cell sorter (FACS), such as those manufactured by Becton-Dickinson under the names FACScan or FACSCalibur. By means of this technique, the cells having a CD45 marker thereon are tagged with a particular fluorescent dye by means of an anti-CD45 antibody which has been conjugated to such a dye. Similarly, the VEGFR marker of the cells are tagged with a different fluorescent dye by means of an anti-VEGFR antibody which is conjugated to the other dye. When the stained cells are placed on the instrument, a stream of cells is directed through an argon laser beam that excites the fluorochrome to emit light. This emitted light is detected by a photo-multiplier tube (PMT) specific for the emission wavelength of the fluorochrome by virtue of a set of optical filters. The signal detected by the PMT is amplified in its own channel and displayed by a computer in a variety of different forms—e.g., a histogram, dot display, or contour display. Thus, fluorescent cells which emit at one wavelength, express a molecule that is reactive with the specific fluorochrome-labeled reagent, whereas non-fluorescent cells or fluorescent cells which emit at a different wavelength do not express this molecule but may express the molecule which is reactive with the fluorochrome-labeled reagent which fluoresces at the other wavelength. The flow cytometer is also semi-quantitative in that it displays the amount of fluorescence (fluorescence intensity) expressed by the cell. This correlates, in a relative sense, to the number of the molecules expressed by the cell.

Flow cytometers can also be equipped to measure non-fluorescent parameters, such as cell volume or light scattered by the cell as it passes through the laser beam. Cell volume is usually a direct measurement. The light scatter PMTs detect light scattered by the cell either in a forward angle (forward scatter; FSC) or at a right angle (side scatter; SSC). FSC is usually an index of size, whereas SSC is an index of cellular complexity, although both parameters can be influenced by other factors.

Preferably, the flow cytometer is equipped with more than one PMT emission detector. The additional PMTs may detect other emission wavelengths, allowing simultaneous detection of more than one fluorochrome, each in individual separate channels. Computers allow the analysis of each channel or the correlation of each parameter with another. Fluorochromes which are typically used with FACS machines include fluorescein isothiocyanate (FITC), which has an emission peak at 525 nm (green), R-phycoerythrin (PE), which has an emission peak at 575 nm (orange-red), propidium iodide (PI), which has an emission peak at 620 nm (red), 7-aminoactinomycin D (7-AAD), which has an emission peak at 660 nm (red), R-phycoerythrin Cy5 (RPE-Cy5), which has an emission peak at 670 nm (red), and allophycocyanin (APC), which has an emission peak at 655-750 nm (deep red).

These and other types of FACS machines may have the additional capability to physically separate the various fractions by deflecting the cells of different properties into different containers.

Any other method for isolating the CD45+ VEGFR+ population of a starting material, such as bone marrow, peripheral blood or cord blood, may also be used in accordance with the present disclosure. The various subpopulations (e.g., CD14+, Tie2+, CD144−) of the present disclosure may be isolated in similar manners.

Either before or after the crude cell populations are purified as described above, the population of progenitor cells may be further concentrated by methods known in the art. For example, the progenitor cells can be enriched by positive selection for one or more antigens characteristic of EPCs. Such antigens include, for example, CD14 or Tie-2.

In one embodiment, blood is withdrawn directly from the circulating peripheral blood of a donor. The blood is percolated continuously through a column containing the solid phase-linked binding molecule, such as an antibody VEGFR-2, to capture EPCs. The progenitor cell-depleted blood is returned immediately to the donor's circulatory system by methods known in the art, such as hemapheresis. The blood is processed in this way until a sufficient number of progenitor cells binds to the column. The stem cells are then isolated from the column by methods known in the art. This method allows rare peripheral blood progenitor cells to be harvested from a very large volume of blood, sparing the donor the expense and pain of harvesting bone marrow and the associated risks of anesthesia, analgesia, blood transfusion, and infection.

EPCs are cultivated and proliferated using the methods described herein. Cells are obtained peripheral blood by isolating peripheral blood mononuclear cells (PBMC) by density gradient centrifugation.

Cell suspensions are seeded in any receptacle capable of sustaining cells, particularly culture flasks, culture plates or roller bottles, and more particularly in small culture flasks such as 25 cm$^2$ culture flasks. Cells cultured in suspension are resuspended at approximately $5 \times 10^4$ to $2 \times 10^5$ cells/ml (for example, $1 \times 10^5$ cells/ml). Cells plated on a fixed substrate are plated at approximately $2\text{-}3 \times 10^3$ cells/cm$^2$. Optionally, the culture plates are coated with a matrix protein such as collagen. The cells can be placed into any known culture medium capable of supporting cell growth, including HEM, DMEM, RPMI, F-12, and the like, containing supplements which are required for cellular metabolism such as glutamine and other amino acids, vitamins, minerals and proteins such as transferrin and the like. The culture medium may also contain antibiotics to prevent contamination with yeast, bacteria and fungi such as penicillin, streptomycin, gentamicin and the like. The culture medium may contain serum derived from bovine, equine, chicken and the like.

Conditions for culturing should be close to physiological conditions. The pH of the culture medium should be close to physiological pH. (for example, between pH 6-8, between about pH 7 to 7.8, or at pH 7.4). Physiological temperatures range between about 30° C. to 40° C. EPCs are cultured at temperatures between about 32° C. to about 38° C. (for example, between about 35° C. to about 37° C.).

Optionally, the culture medium is supplemented with at least one proliferation-inducing ("mitogenic") growth factor. A "growth factor" is protein, peptide or other molecule having a growth, proliferation-inducing, differentiation-inducing, or trophic effect on EPCs. "Proliferation-inducing growth factors" are trophic factor that allows EPCs to proliferate, including any molecule that binds to a receptor on the surface of the cell to exert a trophic, or growth-inducing effect on the cell. Proliferation-inducing growth factors include EGF, amphiregulin, acidic fibroblast growth factor (aFGF or FGF-1), basic fibroblast growth factor (bFGF or FGF-2), transforming growth factor alpha (TGFα), VEGF and combinations thereof. Growth factors are usually added to the culture medium at concentrations ranging between about 1 fg/ml to 1 mg/ml. Concentrations between about 1 to 100 ng/ml are usually sufficient. Simple titration assays can easily be performed to determine the optimal concentration of a particular growth factor.

The biological effects of growth and trophic factors are generally mediated through binding to cell surface receptors. The receptors for a number of these factors have been identified and antibodies and molecular probes for specific receptors are available. EPCs can be analyzed for the presence of growth factor receptors at all stages of differentiation. In many cases, the identification of a particular receptor provides guidance for the strategy to use in further differentiating the cells along specific developmental pathways with the addition of exogenous growth or trophic factors.

Generally, after about 3-10 days in vitro, the culture medium of EPCs is replenished by aspirating the medium, and adding fresh medium to the culture flask. Optionally, the aspirated medium is collected, filtered and used as a condition medium to subsequently passage EPCs. For example the 10%, 20%, 30%, 40% or more condition medium is used.

The EPC cell culture can be easily passaged to reinitiate proliferation. For example, after 3-7 days in vitro, the culture flasks are shaken well and EPCs are then transferred to a 50 ml centrifuge tube and centrifuged at low speed. The medium is aspirated, the EPCs are resuspended in a small amount of culture medium. The cells are then counted and replated at the desired density to reinitiate proliferation. This procedure can be repeated weekly to result in a logarithmic increase in the number of viable cells at each passage. The procedure is continued until the desired number of EPCs is obtained.

EPCs and EPC progeny can be cryopreserved by any method known in the art until they are needed. (See, e.g., U.S. Pat. No. 5,071,741, PCT International patent applications WO93/14191, WO95/07611, WO96/27287, WO96/29862, and WO98/14058, Karlsson et al., 65 Biophysical J. 2524-2536 (1993)). The EPCs can be suspended in an isotonic solution, preferably a cell culture medium, containing a particular cryopreservant. Such cryopreservants include dimethyl sulfoxide (DMSO), glycerol and the like. These cryopreservants are used at a concentration of 5-15% (for example, 8-10%). Cells are frozen gradually to a temperature of −10° C. to −150° C. (for example, −20° C. to −100° C., or −70° C. to −80° C.).

F. Genetic modification of the cells

In one embodiment, the cells of the present disclosure, MSCs and/or EPCs, are genetically modified. In one aspect, such genetic modification enhances the therapeutic activity of the cells. Non-limiting examples of such modification include enhanced expression or activation of an endothelial nitric oxide synthase (eNOS), heme oxygenase (HMOX1) and prostacyclin synthase (PTGIS).

In one aspect, the cell is transformed with a nucleic acid that increases the expression of biological activity of a protein selected from the group consisting of endothelial nitric oxide synthase (eNOS), heme oxygenase (HMOX1) and prostacyclin synthase (PTGIS). In one aspect, the nucleic acid encodes the protein.

In some aspects, the cells are genetically modified to produce a heterologous protein. Sometimes, the cells will be genetically modified such that the heterologous protein is secreted from the cells. However, in an embodiment the cells can be modified to express a functional non-protein encoding polynucleotide such as dsRNA (typically for RNA silencing), an antisense oligonucleotide or a catalytic nucleic acid (such as a ribozyme or DNAzyme).

Genetically modified cells may be cultured in the presence of at least one cytokine in an amount sufficient to support growth of the modified cells. The genetically modified cells thus obtained may be used immediately (e.g., in transplant), cultured and expanded in vitro, or stored for later uses. The modified cells may be stored by methods well known in the art, e.g., frozen in liquid nitrogen.

Genetic modification as used herein encompasses any genetic modification method which involves introduction of an exogenous or foreign polynucleotide into a cell described herein or modification of an endogenous gene within the cell. Genetic modification includes but is not limited to transduction (viral mediated transfer of host DNA from a host or donor to a recipient, either in vitro or in vivo), transfection (transformation of cells with isolated viral DNA genomes), liposome mediated transfer, electroporation, calcium phosphate transfection or coprecipitation and others. Methods of transduction include direct co-culture of cells with producer cells (Bregni et al., 1992) or culturing with viral supernatant alone with or without appropriate growth factors and polycations.

An exogenous polynucleotide is preferably introduced to the cell in a vector. The vector preferably includes the necessary elements for the transcription and translation of the inserted coding sequence. Methods used to construct such vectors are well known in the art. For example, techniques for constructing suitable expression vectors are described in detail in Sambrook et al., Molecular Cloning: A Laboratory Manual, Cold Spring Harbor Press, N.Y. (3rd Ed., 2000); and Ausubel et al., Current Protocols in Molecular Biology, John Wiley & Sons, Inc., New York (1999).

Vectors may include, but are not limited to, viral vectors, such as retroviruses, adenoviruses, adeno-associated viruses, and herpes simplex viruses; cosmids; plasmid vectors; synthetic vectors; and other recombination vehicles typically used in the art. Vectors containing both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). Specific examples include, pSG, pSV2CAT, pXtl from Stratagene; and pMSG, pSVL, pBPV and pSVK3 from Pharmacia.

Vectors can include retroviral vectors (see, Coffin et al., "Retroviruses", Chapter 9 pp; 437-473, Cold Springs Harbor Laboratory Press, 1997). Vectors useful in the disclosure can be produced recombinantly by procedures well known in the art. For example, WO94/29438, WO97/21824 and WO97/21825 describe the construction of retroviral packaging plasmids and packing cell lines. Exemplary vectors include the pCMV mammalian expression vectors, such as pCMV6b and pCMV6c (Chiron Corp.), pSFFV-Neo, and pBluescript-Sk+. Non-limiting examples of useful retroviral vectors are those derived from murine, avian or primate retroviruses. Common retroviral vectors include those based on the Moloney murine leukemia virus (MoMLV-vector). Other MoMLV derived vectors include, Lmily, LINGFER, MIN-GFR and MINT. Additional vectors include those based on Gibbon ape leukemia virus (GAIN) and Moloney murine sarcoma virus (MOMSV) and spleen focus forming virus (SFFV). Vectors derived from the murine stem cell virus (MESV) include MESV-MiLy. Retroviral vectors also include vectors based on lentiviruses, and non-limiting examples include vectors based on human immunodeficiency virus (HIV-1 and HIV-2).

In producing retroviral vector constructs, the viral gag, pol and env sequences can be removed from the virus, creating room for insertion of foreign DNA sequences. Genes encoded by foreign DNA are usually expressed under the control a strong viral promoter in the long terminal repeat (LTR). Selection of appropriate control regulatory sequences is dependent on the host cell used and selection is within the skill of one in the art. Numerous promoters are known in addition to the promoter of the LTR. Non-limiting examples include the phage lambda PL promoter, the human cytomegalovirus (CMV) immediate early promoter; the U3 region promoter of the Moloney Murine Sarcoma Virus (MMSV), Rous Sacroma Virus (RSV), or Spleen Focus Forming Virus (SFFV); Granzyme A promoter; and the Granzyme B promoter. Additionally inducible or multiple control elements may be used. The selection of a suitable promoter will be apparent to those skilled in the art.

Such a construct can be packed into viral particles efficiently if the gag, pol and env functions are provided in trans by a packing cell line. Therefore, when the vector construct is introduced into the packaging cell, the gag-pol and env proteins produced by the cell, assemble with the vector RNA to produce infectious virons that are secreted into the culture medium. The virus thus produced can infect and integrate into the DNA of the target cell, but does not produce infectious viral particles since it is lacking essential packaging sequences. Most of the packing cell lines currently in use have been transfected with separate plasmids, each containing one of the necessary coding sequences, so that multiple recombination events are necessary before a replication competent virus can be produced. Alternatively the packaging cell line harbours a provirus. The provirus has been crippled so that although it may produce all the proteins required to assemble infectious viruses, its own RNA cannot be packaged into virus. RNA produced from the recombinant virus is packaged instead. Therefore, the virus stock released from the packaging cells contains only recombinant virus. Non-limiting examples of retroviral packaging lines include PA12, PA317, PE501, PG13, PSICRIP, RDI 14, GP7C-tTA-G10, ProPak-A (PPA-6), and PT67.

Other suitable vectors include adenoviral vectors (see, WO 95/27071) and adeno-associated viral vectors. These vectors are all well known in the art, e.g., as described in Stem Cell Biology and Gene Therapy, eds. Quesenberry et al., John Wiley & Sons, 1998; and U.S. Pat. Nos. 5,693,531 and 5,691,176. The use of adenovirus-derived vectors may be advantageous under certain situation because they are not capable of infecting non-dividing cells. Unlike retroviral DNA, the adenoviral DNA is not integrated into the genome of the target cell. Further, the capacity to carry foreign DNA is much larger in adenoviral vectors than retroviral vectors. The adeno-associated viral vectors are another useful delivery system. The DNA of this virus may be integrated into non-dividing cells, and a number of polynucleotides have been successful introduced into different cell types using adeno-associated viral vectors.

In some embodiments, the construct or vector will include two or more heterologous polynucleotide sequences. Preferably the additional nucleic acid sequence is a polynucleotide which encodes a selective marker, a structural gene, a therapeutic gene, or a cytokine/chemokine gene.

A selective marker may be included in the construct or vector for the purposes of monitoring successful genetic modification and for selection of cells into which DNA has been integrated. Non-limiting examples include drug resistance markers, such as G148 or hygromycin. Additionally negative selection may be used, for example wherein the marker is the HSV-tk gene. This gene will make the cells sensitive to agents such as acyclovir and gancyclovir. The NeoR (neomycin/G148 resistance) gene is commonly used but any convenient marker gene may be used whose gene sequences are not already present in the target cell can be used. Further non-limiting examples include low-affinity Nerve Growth Factor (NGFR), enhanced fluorescent green protein (EFGP), dihydrofolate reductase gene (DHFR) the bacterial hisD gene, murine CD24 (HSA), murine CD8a (lyt), bacterial genes which confer resistance to puromycin or phleomycin, and .beta.-glactosidase.

The additional polynucleotide sequence(s) may be introduced into the cell on the same vector or may be introduced into the host cells on a second vector. In a preferred embodiment, a selective marker will be included on the same vector as the polynucleotide.

The present disclosure also encompasses genetically modifying the promoter region of an endogenous gene such that expression of the endogenous gene is up-regulated resulting in the increased production of the encoded protein compared to a wild type cell.

G. Pharmaceutical compositions and administration methods

One embodiment of the present disclosure provides a pharmaceutical composition comprising a therapeutically effective amount of a mesenchymal stem cell (MSC) or a MSC-conditioned culture medium and a prostacyclin and a pharmaceutically acceptable carrier. In one aspect, the composition further comprises an endothelial progenitor cell (EPC).

In one aspect, the pharmaceutical composition further comprises at least one pharmaceutically-acceptable carrier. The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically-acceptable carrier" as used herein means a pharmaceutically-acceptable material, composition or vehicle, such as a liquid or solid filler, diluent, excipient, or solvent encapsulating material.

Pharmaceutically acceptable carriers include saline, aqueous buffer solutions, solvents and/or dispersion media. The use of such carriers are well known in the art. The solution is preferably sterile and fluid to the extent that easy syringability exists. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like.

Some examples of materials and solutions which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The pharmaceutical compositions useful for the methods of the disclosure may comprise a polymeric carrier or extracellular matrix.

A variety of biological or synthetic solid matrix materials (i.e., solid support matrices, biological adhesives or dressings, and biological/medical scaffolds) are suitable for use in this disclosure. The matrix material is preferably medically acceptable for use in in vivo applications. Non-limiting examples of such medically acceptable and/or biologically or physiologically acceptable or compatible materials include, but are not limited to, solid matrix materials that are absorbable and/or non-absorbable, such as small intestine submucosa (SIS), e.g., porcine-derived (and other SIS sources); crosslinked or non-crosslinked alginate, hydrocolloid, foams, collagen gel, collagen sponge, polyglycolic acid (PGA) mesh, polyglactin (PGL) mesh, fleeces, foam dressing, bioadhesives (e.g., fibrin glue and fibrin gel) and dead de-epidermized skin equivalents in one or more layers.

Fibrin glues are a class of surgical sealants which have been used in various clinical settings. As the skilled address would be aware, numerous sealants are useful in compositions for use in the methods of the disclosure. However, a preferred embodiment of the disclosure relates to the use of fibrin glues with the cells described herein.

When used herein the term "fibrin glue" refers to the insoluble matrix formed by the cross-linking of fibrin polymers in the presence of calcium ions. The fibrin glue may be formed from fibrinogen, or a derivative or metabolite thereof, fibrin (soluble monomers or polymers) and/or complexes thereof derived from biological tissue or fluid which forms a fibrin matrix. Alternatively, the fibrin glue may be formed from fibrinogen, or a derivative or metabolite thereof, or fibrin, produced by recombinant DNA technology.

The fibrin glue may also be formed by the interaction of fibrinogen and a catalyst of fibrin glue formation (such as thrombin and/or Factor XIII). As will be appreciated by those skilled in the art, fibrinogen is proteolytically cleaved in the presence of a catalyst (such as thrombin) and converted to a fibrin monomer. The fibrin monomers may then form polymers which may cross-link to form a fibrin glue matrix. The cross-linking of fibrin polymers may be enhanced by the presence of a catalyst such as Factor XIII The catalyst of fibrin glue formation may be derived from blood plasma, cryoprecipitate or other plasma fractions containing fibrinogen or thrombin. Alternatively, the catalyst may be produced by recombinant DNA technology.

The rate at which the clot forms is dependent upon the concentration of thrombin mixed with fibrinogen. Being an enzyme dependent reaction, the higher the temperature (up to 37.degree. C.) the faster the clot formation rate. The tensile strength of the clot is dependent upon the concentration of fibrinogen used.

Use of fibrin glue and methods for its preparation and use are described in U.S. Pat. No. 5,643,192. U.S. Pat. No. 5,643,192 discloses the extraction of fibrinogen and thrombin components from a single donor, and the combination of only these components for use as a fibrin glue. U.S. Pat. No. 5,651,982, describes another preparation and method of use for fibrin glue. U.S. Pat. No. 5,651,982, provides a fibrin glue with liposomes for use as a topical sealant in mammals.

Several publications describe the use of fibrin glue for the delivery of therapeutic agents. For example, U.S. Pat. No. 4,983,393 discloses a composition for use as an intra-vaginal insert comprising agarose, agar, saline solution glycosaminoglycans, collagen, fibrin and an enzyme. Further, U.S. Pat. No. 3,089,815 discloses an injectable pharmaceutical preparation composed of fibrinogen and thrombin and U.S. Pat. No. 6,468,527 discloses a fibrin glue which facilitates the delivery of various biological and non-biological agents to specific sites within the body. Such procedures can be used in the methods of the disclosure.

Suitable polymeric carriers include porous meshes or sponges formed of synthetic or natural polymers, as well as polymer solutions. One form of matrix is a polymeric mesh or sponge; the other is a polymeric hydrogel. Natural polymers that can be used include proteins such as collagen, albumin, and fibrin; and polysaccharides such as alginate and polymers of hyaluronic acid. Synthetic polymers include both biodegradable and non-biodegradable polymers. Examples of biodegradable polymers include polymers of hydroxy acids such as polylactic acid (PLA), polyglycolic acid (PGA), and polylactic acid-glycolic acid (PLGA), polyorthoesters, polyanhydrides, polyphosphazenes, and combinations thereof. Non-biodegradable polymers include polyacrylates, polymethacrylates, ethylene vinyl acetate, and polyvinyl alcohols.

Polymers that can form ionic or covalently crosslinked hydrogels which are malleable are used to encapsulate cells. A hydrogel is a substance formed when an organic polymer (natural or synthetic) is cross-linked via covalent, ionic, or hydrogen bonds to create a three-dimensional open-lattice structure which entraps water molecules to form a gel. Examples of materials which can be used to form a hydrogel include polysaccharides such as alginate, polyphosphazines, and polyacrylates, which are crosslinked ionically, or block copolymers such as Pluronics™ or Tetronics™, polyethylene oxide-polypropylene glycol block copolymers which are crosslinked by temperature or pH, respectively. Other materials include proteins such as fibrin, polymers such as polyvinylpyrrolidone, hyaluronic acid and collagen.

In general, these polymers are at least partially soluble in aqueous solutions, such as water, buffered salt solutions, or aqueous alcohol solutions, that have charged side groups, or a monovalent ionic salt thereof. Examples of polymers with acidic side groups that can be reacted with cations are poly(phosphazenes), poly(acrylic acids), poly(methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups. Examples of polymers with basic side groups that can be reacted with anions are poly(vinyl amines), poly(vinyl pyridine), poly(vinyl imidazole), and some imino substituted polyphosphazenes. The ammonium or quaternary salt of the polymers can also be formed from the backbone nitrogens or pendant imino groups. Examples of basic side groups are amino and imino groups.

Further, a composition used for a method of the disclosure may comprise at least one therapeutic agent. For example, the composition may contain an analgesic to aid in treating inflammation or pain, or an anti-infective agent to prevent infection of the site treated with the composition. More specifically, non-limiting examples of useful therapeutic agents include the following therapeutic categories: analgesics, such as nonsteroidal anti-inflammatory drugs, opiate agonists and salicylates; anti-infective agents, such as antihelmintics, antianaerobics, antibiotics, aminoglycoside antibiotics, antifungal antibiotics, cephalosporin antibiotics, macrolide antibiotics, miscellaneous .beta.-lactam antibiotics, penicillin antibiotics, quinolone antibiotics, sulfonamide antibiotics, tetracycline antibiotics, antimycobacterials, antituberculosis antimycobacterials, antiprotozoals, antimalarial antiprotozoals, antiviral agents, anti-retroviral agents, scabicides, anti-inflammatory agents, corticosteroid anti-inflammatory agents, antipruritics/local anesthetics, topical anti-infectives, antifungal topical anti-infectives, antiviral topical anti-infectives; electrolytic and renal agents, such as acidifying agents, alkalinizing agents, diuretics, carbonic anhydrase inhibitor diuretics, loop diuretics, osmotic diuretics, potassium-sparing diuretics, thiazide diuretics, electrolyte replacements, and uricosuric agents; enzymes, such as pancreatic enzymes and thrombolytic enzymes; gastrointestinal agents, such as antidiarrheals, gastrointestinal anti-inflammatory agents, gastrointestinal anti-inflammatory agents, antacid anti-ulcer agents, gastric acid-pump inhibitor anti-ulcer agents, gastric mucosal anti-ulcer agents, H2-blocker anti-ulcer agents, cholelitholytic agent's, digestants, emetics, laxatives and stool softeners, and prokinetic agents; general anesthetics, such as inhalation anesthetics, halogenated inhalation anesthetics, intravenous anesthetics, barbiturate intravenous anesthetics, benzodiazepine intravenous anesthetics, and opiate agonist intravenous anesthetics; hormones and hormone modifiers, such as abortifacients, adrenal agents, corticosteroid adrenal agents, androgens, anti-androgens, immunobiologic agents, such as immunoglobulins, immunosuppressives, toxoids, and vaccines; local anesthetics, such as amide local anesthetics and ester local anesthetics; musculoskeletal agents, such as anti-gout anti-inflammatory agents, corticosteroid anti-inflammatory agents, gold compound anti-inflammatory agents, immunosuppressive anti-inflammatory agents, nonsteroidal anti-inflammatory drugs (NSAIDs), salicylate anti-inflammatory agents, minerals; and vitamins, such as vitamin A, vitamin B, vitamin C, vitamin D, vitamin E, and vitamin K.

Compositions useful for the methods of the present disclosure may include cell culture components, e.g., culture media including amino acids, metals, coenzyme factors, as well as small populations of other cells, e.g., some of which may arise by subsequent differentiation of the stem cells.

Compositions useful for the methods of the present disclosure may be prepared, for example, by sedimenting out the subject cells from the culture medium and re-suspending them in the desired solution or material. The cells may be sedimented and/or changed out of the culture medium, for example, by centrifugation, filtration, ultrafiltration, etc.

The skilled artisan can readily determine the amount of cells and optional carrier(s) in compositions and to be administered in methods of the disclosure. In an embodiment, any additives (in addition to the active cell(s)) are present in an amount of 0.001 to 50% (weight) solution in phosphate buffered saline, and the active ingredient is present in the order of micrograms to milligrams, such as about 0.0001 to about 5 wt %, preferably about 0.0001 to about 1 wt %, still more preferably about 0.0001 to about 0.05 wt % or about 0.001 to about 20 wt %, preferably about 0.01 to about 10 wt %, and still more preferably about 0.05 to about 5 wt %. Of course, for any composition to be administered to an animal or human, and for any particular method of administration, it is preferred to determine therefore: toxicity, such as by determining the lethal dose (LD) and LD50 in a suitable animal model e.g., rodent such as mouse; and, the dosage of the composition(s), concentration of components therein and timing of administering the composition (s), which elicit a suitable response. Such determinations do not require undue experimentation from the knowledge of the skilled artisan, this disclosure and the documents cited herein. And, the time for sequential administrations can be ascertained without undue experimentation.

Compositions useful for the methods of the present disclosure can be administered via, inter alia, localized injection, including catheter administration, systemic injection, localized injection, intravenous injection, intrauterine injection or parenteral administration. When administering a therapeutic composition described herein (e.g., a pharmaceutical composition), it will generally be formulated in a unit dosage injectable form (solution, suspension, emulsion).

According to one embodiment of the present disclosure, the compositions can be co-administered with at least one other medicine for vasculopathy, which comprises prostaglandin 12 ($PGI_2$), prostacyclin analogues, phosphodiesterase-5 (PDE-5) inhibitor, endothelin receptor antagonist (ETRA), tyrosine kinase inhibitors, and soluble guanylate cyclase stimulator.

According to one embodiment of the present disclosure, the method for treating vasculopathy may further comprises reducing thrombosis in pulmonary arteries; reducing inflammation in pulmonary arteries; reducing the proliferation of intimal smooth muscle in pulmonary arteries; reducing the formation of plexiform lesions in pulmonary arteries; increasing the amount of nitric oxide in pulmonary arteries; increasing the amount of $PGI_2$ in pulmonary arteries; reducing the level of Endothelin-1 in pulmonary arteries; reducing the amount of growth factors in pulmonary arteries; or promoting proper endothelial morphology in pulmonary arteries.

Treating vasculopathy by administering/transplanting progenitor cells are described in Wang et al., J. Am. Coll. Cardiol. 49:1566-71 (2007), Zhao et al. Circ. Res. 96:442-450 (2005), and Nagaya et al., Circulation 108:889-895 (2003), the content of which are hereby incorporated by reference in their entireties.

Administration/transplantation of cells into the damaged blood vessels has the potential to repair damaged vascular tissue, e.g., veins, arteries, capillaries, thereby restoring vascular function. However, the absence of suitable cells for transplantation purposes has prevented the full potential of this procedure from being met. "Suitable" cells are cells that meet one or more of the following criteria: (1) can be obtained in large numbers; (2) can be proliferated in vitro to allow insertion of genetic material, if necessary; (3) capable of surviving indefinitely and facilitate vascular repair on transplantation r; and (4) are non-immunogenic, preferably obtained from a patient's own tissue or from a compatible donor. Suitable cells may be autologous, allogeneic or xenogeneic.

The cells can be administered to a subject with abnormal vasculature or coronary failure symptoms. The cells can be prepared from the recipient's own blood or bone marrow. In such instances the EPCs can be generated from dissociated tissue and proliferated in vitro using the methods described above. Upon suitable expansion of cell numbers, the EPCs may be harvested, genetically modified if necessary, and readied for direct injection into the recipient's vasculature The cells can be prepared from donor tissue that is xenogeneic to the host. For xenografts to be successful, some method of reducing or eliminating the immune response to the implanted tissue is usually employed. Thus the recipients can be immunosuppressed, either through the use of immunosuppressive drugs such as cyclosporin, or through local immunosuppression strategies employing locally applied immunosuppressants. Local immunosuppression is disclosed by Gruber, 54 Transplantation 1-11 (1992). U.S. Pat. No. 5,026,365 discloses encapsulation methods suitable for local immunosuppression.

As an alternative to employing immunosuppression techniques, methods of gene replacement or knockout using homologous recombination in embryonic stem cells, taught by Smithies et al., 317 Nature 230-234 (1985), and extended to gene replacement or knockout in cell lines (Zheng et al., 88 Proc. Natl. Acad. Sci. 8067-8071 (1991)), can be applied to EPCs for the ablation of major histocompatibility complex (MHC) genes. EPCs lacking MHC expression allows for the grafting of enriched endothelial cell populations across allogeneic, and perhaps even xenogeneic, histocompatibility barriers without the need to immunosuppress the recipient. General reviews and citations for the use of recombinant methods to reduce antigenicity of donor cells are also disclosed by Gruber, 54 Transplantation 1-11 (1992). Exemplary approaches to the reduction of immunogenicity of transplants by surface modification are disclosed by PCT International patent application WO 92/04033 and PCT/US99/24630. Alternatively the immunogenicity of the graft may be reduced by preparing EPCs from a transgenic animal that has altered or deleted MHC antigens.

The cells can be encapsulated and used to deliver factors to the host, according to known encapsulation technologies, including microencapsulation (see, e.g., U.S. Pat. Nos. 4,352,883; 4,353,888; and 5,084,350, herein incorporated by reference) and macroencapsulation (see, e.g. U.S. Pat. Nos. 5,284,761, 5,158,881, 4,976,859 and 4,968,733 and PCT International patent applications WO 92/19195 and WO 95/05452, each incorporated herein by reference). Macroencapsulation is described in U.S. Pat. Nos. 5,284,761; 5,158,881; 4,976,859; 4,968,733; 5,800,828 and PCT International patent application WO 95/05452, each incorporated herein by reference. Multiple macroencapsulation devices can be implanted in the host.

Cells prepared from tissue that is allogeneic to that of the recipient can be tested for use by the well-known methods of tissue typing, to closely match the histocompatibility type of the recipient.

Cells administered to the vasculature can form a vascular graft, so that the cells form normal connections with neighboring vascular cells, maintaining contact with transplanted or existing endothelial cells. Thus the transplanted cells can re-establish the vascular tissue which have been damaged due to disease and aging.

Functional integration of the graft into the host's vascular tissue can be assessed by examining the effectiveness of grafts on restoring various functions.

According to one embodiment of the present disclosure, cells can be co-administered to the recipient with at least one growth factor, such as FGF, VEGF-A, VEGF-B, BMP-4, TGF-Beta, etc.

EXAMPLES

The present technology is further defined by reference to the following non-limiting examples. It will be apparent to those skilled in the art that many modifications, both to compositions and methods, may be practiced without departing from the scope of the current invention.

Example 1. Optimization of Treprostinil Concentration for Cellular Response in BM-MSC This example identifies minimum treprostinil concentrations required to enhance the angiogenic potential of human bone marrow mesenchymal stem cells (BM-MSC).

A single vial of human bone marrow-derived MSC was expanded and seeded into twenty (20) wells of 6-well plates using standard growth medium. At 95-99% confluency, cells were thoroughly washed with phosphate-buffered saline (PBS). Cells were then exposed to media containing 0, 0.1, 1.0, 10, or 100 µg/mL of treprostinil (n=4 wells for each concentration).

After 24 hours of culture, the conditioned media was collected from each replicate and analyzed for Vascular Endothelial Growth Factor (VEGF) protein by enzyme-linked immunosorbent assay (ELISA). The goal of this experiment was to determine the optimal concentration of treprostinil needed to elicit a cellular response in MSC (using VEGF as a read out).

Flow cytometry analysis (FIG. 1) demonstrated that the bone marrow MSC used in this study were positive for MSC markers CD73, CD105, CD90, and HLA-ABC. Cells were negative or low for CD34, CD45, CD14, CD19 and HLA-DR. Definition of MSC was established by the International Society for Cellular Therapy (Dominici et al., Cytotherapy 8(4):315-7, 2006).

Figure 2:
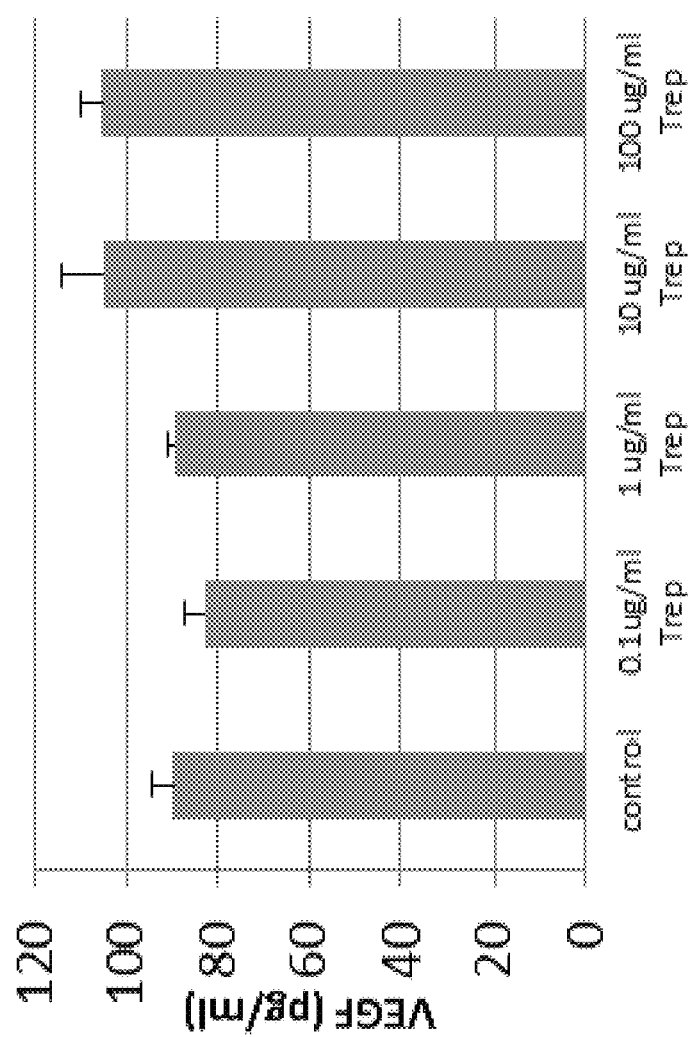
FIG. 2 is a chart showing VEGF secretion by human bone marrow MSC after 24 hours of exposure to treprostinil.

FIG. 2 is a chart showing VEGF secretion by human bone marrow MSC after 24 hours of exposure to treprostinil. Cell culture supernatant was assayed for VEGF by ELISA (n=4 per group). As shown in FIG. 2, no statistically significant differences were observed among the dosage groups (error bars represent the standard deviation of the test group).

This experiment suggests that treprostinil concentrations of 100 µg/mL or less may not significantly enhance the angiogenic potential of human bone marrow MSC. However, there is a slight trend of increased VEGF secretion as treprostinil increased. Subsequent examples investigated higher concentrations of treprostinil.

Example 2. Optimization of Treprostinil Concentration for Cellular Response in BM-MSC This example identifies 250 µg/mL as a good concentration of treprostinil for enhancing the angiogenic potential of human BM-MSC.

A follow-up experiment to Example 1 was conducted to determine if treprostinil concentrations above 100 µg/mL affected MSC secretion of VEGF. As before, a single vial (same lot/batch) of bone marrow-derived MSC was expanded to thirty (30) wells of 6-well plates using standard growth medium. At 95-99% confluency, cells were thoroughly washed with PBS. Cells were then exposed to media containing 0, 100, 200, 300, or 400 µg/mL of treprostinil (n=6 wells for each concentration).

Conditioned media was assayed for VEGF by ELISA after 24 hours of treprostinil exposure (n=4 replicates). Cells from those replicates were lysed, and RNA was extracted to determine VEGF-A gene expression by qRT-PCR. Cells from the remaining two (2) replicates were trypsinized, and assayed for cell viability by trypan blue exclusion.

Figure 3A:
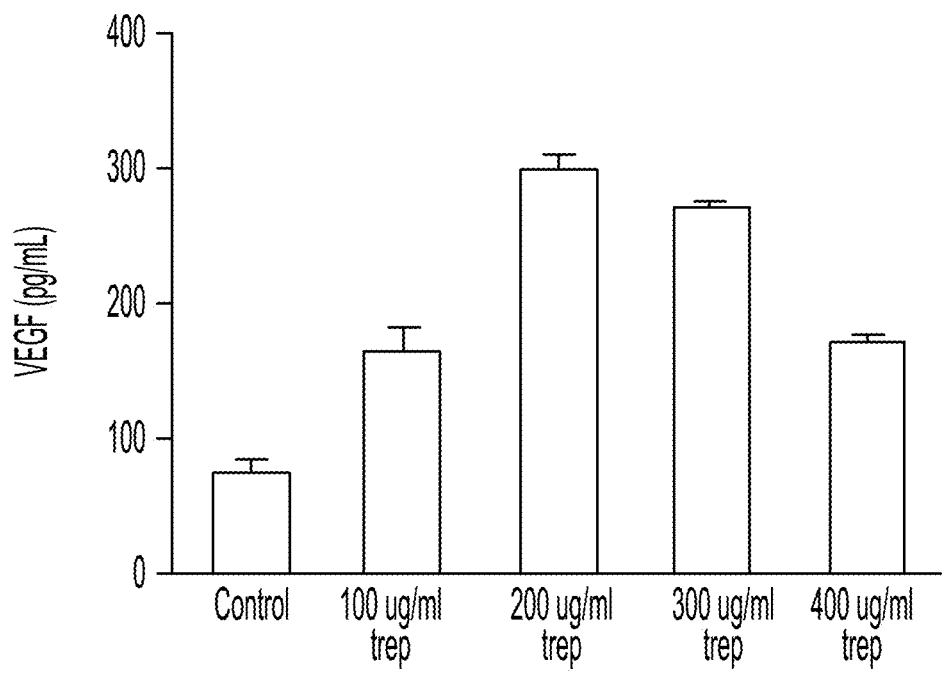
FIG. 3A-3B present a MSC secretion chart (A) and a gene expression chart (B) of VEGF after 24 hours exposure to treprostinil.
Figure 3B:
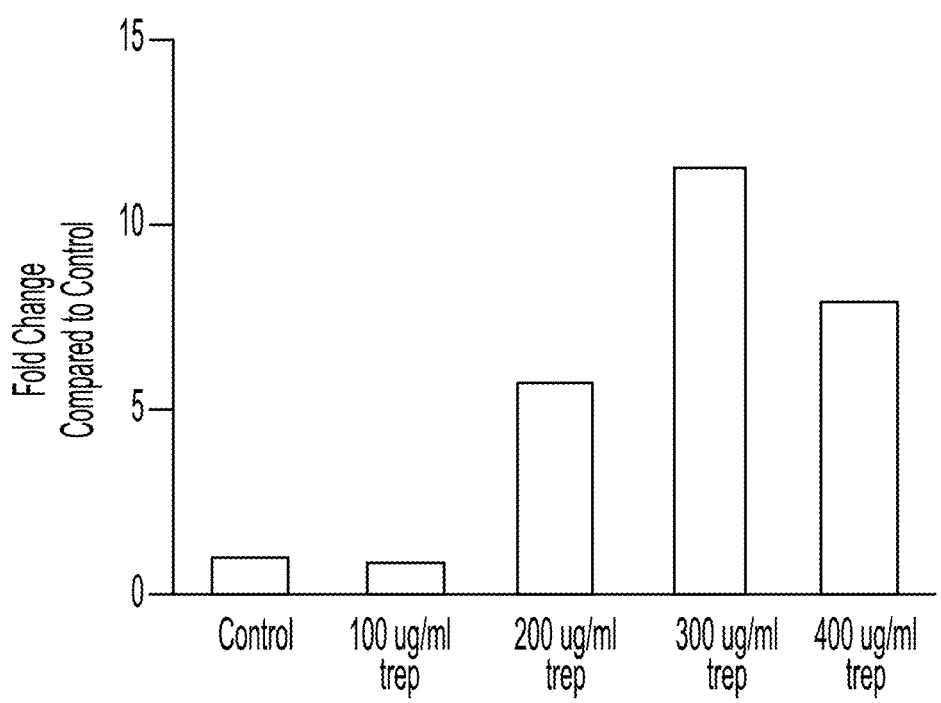

Cell culture supernatant was assayed for VEGF protein by ELISA (FIG. 3A, n=4). Cell lysates from those cultures were assayed for VEGF-A gene expression by qRT-PCR, and normalized to the control value (FIG. 3B, n=4). In both figures, error bars represent the standard deviation in each test group.

Figure 4:
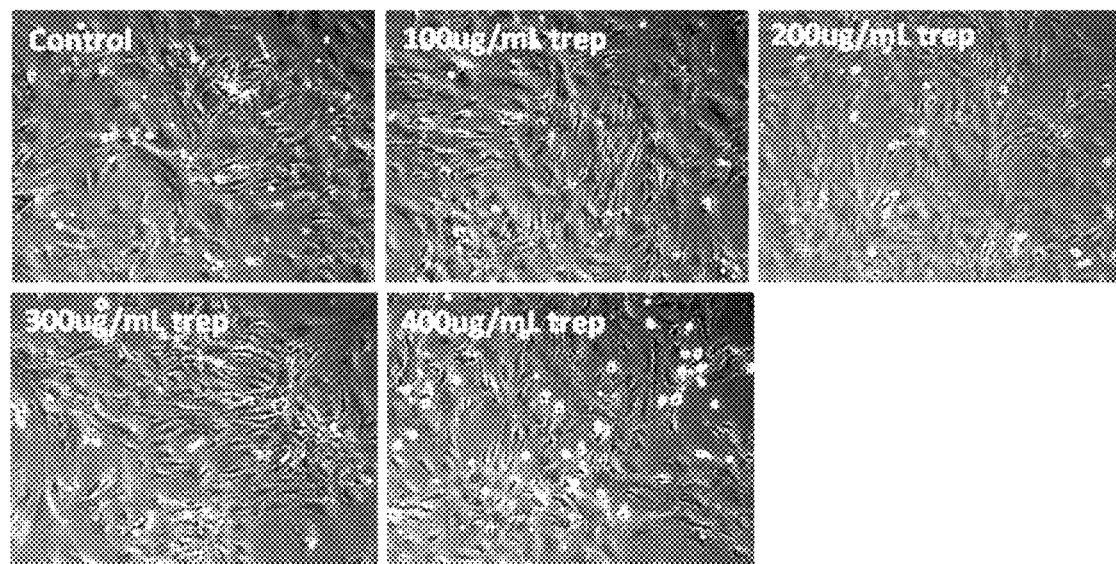
FIG. 4 presents representative images of MSC exposed to increasing concentrations of treprostinil.

FIG. 4 includes representative images of MSC exposed to increasing concentrations of treprostinil. At the highest dose (400 µg/mL), the increased numbers of rounded up, detaching cells suggested a cytotoxic effect of treprostinil on MSC.

Figure 5:
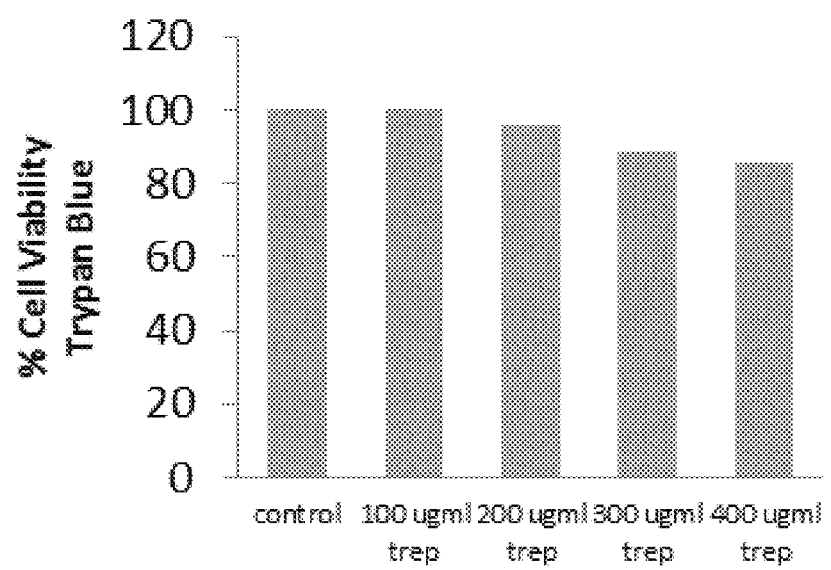
FIG. 5 is chart showing cellular viability of MSC exposed to treprostinil.

MSC were stained with trypan blue to determine the total number of live and dead cells in each well (FIG. 5, n=2 wells per group). Percent viability was calculated as the ratio between trypan blue negative cells and the total population (100×Live/Total). While there were too few replicates to perform statistical analysis, there was a trend of decreased viability as treprostinil concentration increased above 100 µg/mL. However, cell viability did not decrease below 85% at any dose level tested in this experiment.

This example demonstrates that high levels of treprostinil negatively impacted cellular viability of MSC. At 100 µg/mL, VEGF secretion increased ~2-fold, but VEGF-A gene expression was not significantly different from untreated controls after 24 hours of exposure. VEGF-A gene expression did increase over 5-fold at the 200 µg/mL level of treprostinil, and VEGF secretion was observed at ~3-fold of control values. VEGF secretion did not increase above this value, even with higher concentrations of treprostinil, suggesting that the effect was saturated. Therefore, 250 µg/mL was selected as the optimal treprostinil concentration to use in subsequent studies.

Example 3. Comprehensive Analysis of MSC Exposed to 250 µg/mL Treprostinil

Based on the previous examples, this example selected 250 µg/mL as the treprostinil dose to elicit a cellular response in MSC. This concentration was based on increased VEGF production compared to untreated control cells, and minimal cytotoxic effects.

Human bone marrow MSC were expanded and seeded into six (6) T225 flasks using standard growth medium (Table 1). At 95-99% confluency, cells were thoroughly washed with PBS. Three (3) flasks were replenished with basal media containing 250 µg/mL treprostinil, (+)Tre, and the remaining three (3) flasks were replenished with unsupplemented basal media, (−)Tre.

TABLE 1

Study design to evaluate the effects of treprostinil on MSC activity.

| Sample # | Media | Cell analysis | Media analysis |
|---|---|---|---|
| n = 3 | (+)Tre | RNA isolation for gene microarray | Secreted proteins Exosome RNA content |
| n = 3 | (−)Tre | RNA isolated for gene microarray | Secreted proteins, Exosome RNA content |

After 24 hours of culture, representative images were captured from (+) Tre and (−) Tre cultures. Conditioned media was collected from each replicate, divided into two samples of appropriate volumes, and analyzed separately for: 1) secreted proteins (Myriad RBM InflammationMAP® 1.0) and 2) exosome RNA content. Cells were lysed directly from culture flasks, processed for total RNA isolation, and analyzed for gene expression by microarray (Illumina Human HT12 Expression BeadChip).

Figure 6:
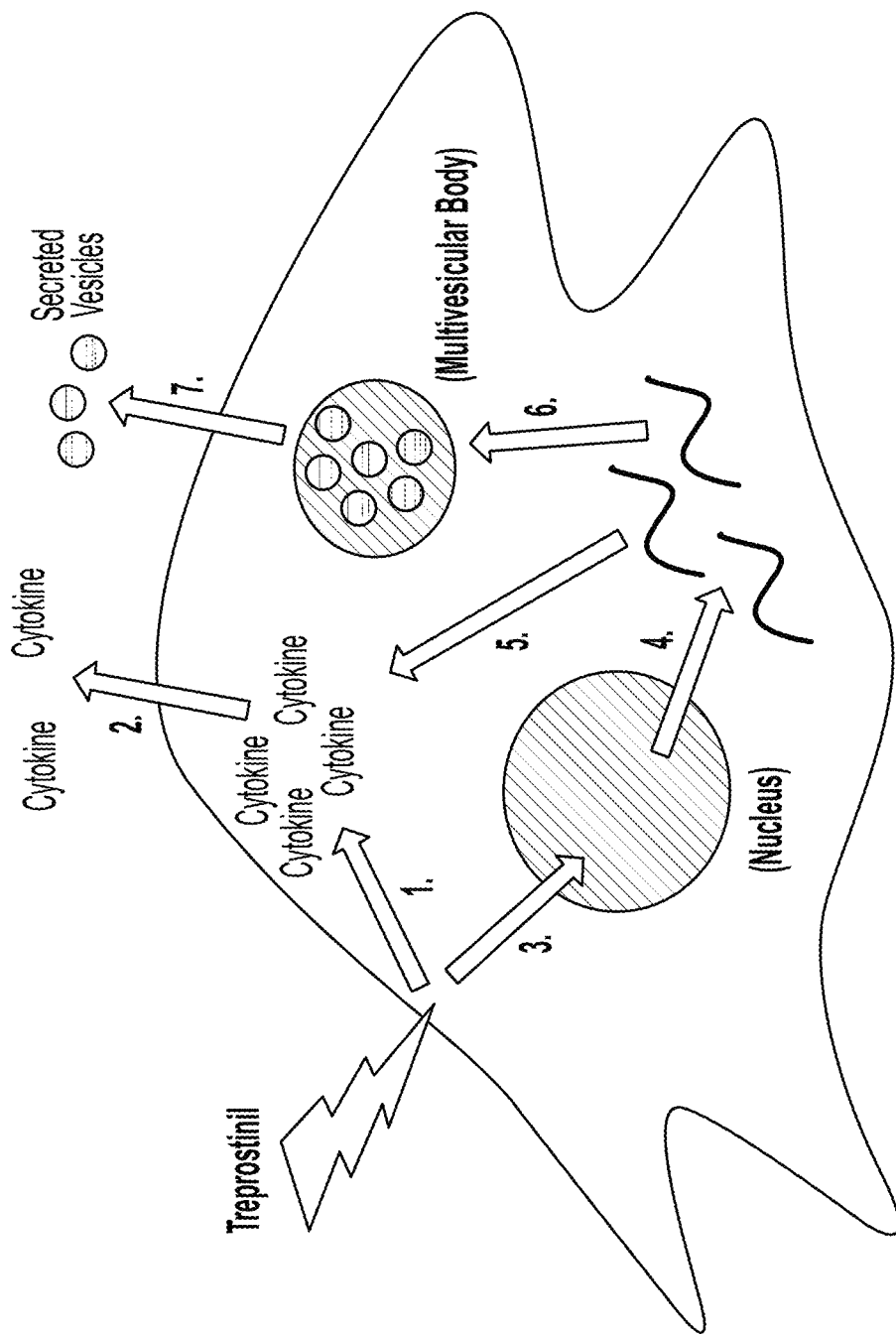
FIG. 6 illustrates a model for the effects of treprostinil on cell signaling, gene expression, and the release of paracrine factors.

FIG. 6 illustrates a model for the effects of treprostinil on cell signaling, gene expression, and the release of paracrine factors, and with the table below showing assays useful to test the effects.

| Cellular function | Assay |
|---|---|
| 1. Intracellular signaling | |
| 2. Cytokine release | Immunoassay |
| 3. Nuclear signaling | |
| 4. RNA expression | RT-PCR, Microarray |
| 5. Protein translation | |
| 6. RNA packaging | |
| 7. Vesicle release | RT-PCR, Particle analysis |

To characterize the effect of treprostinil on MSC, cells were analyzed by qRT-PCR and microarray to identify changes in gene expression (4). Cell culture supernatant media was assayed for selected inflammatory cytokines by bead-based immunoassays (2). Secreted vesicles were isolated from cell culture supernatant, and assayed for RNA content by qRT-PCR (7). Vesicles were also assayed for size and concentration by tunable resistive pulse sensing, or TRPS (7) (refer to Example 4).

Figure 7A:
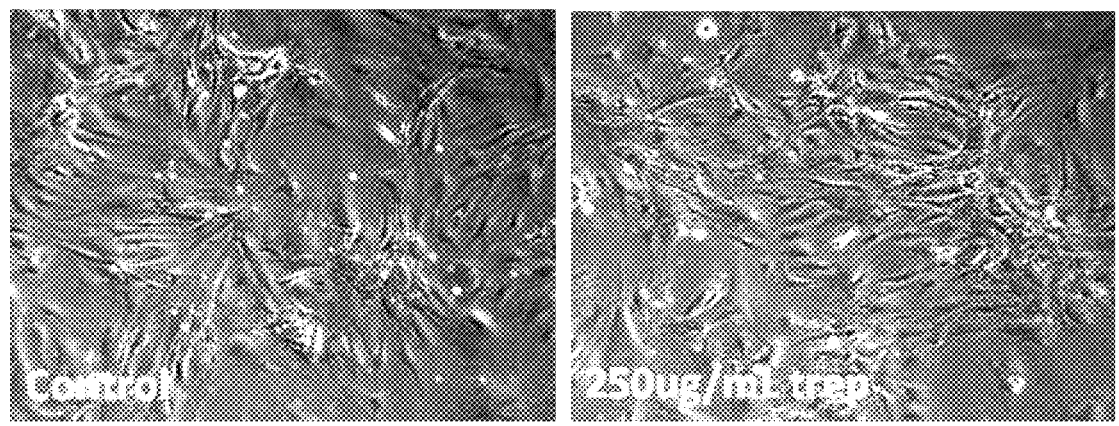
FIG. 7A-7B presents images and a chart showing MSC treated with or without 250 µg/mL treprostinil.
Figure 7B:
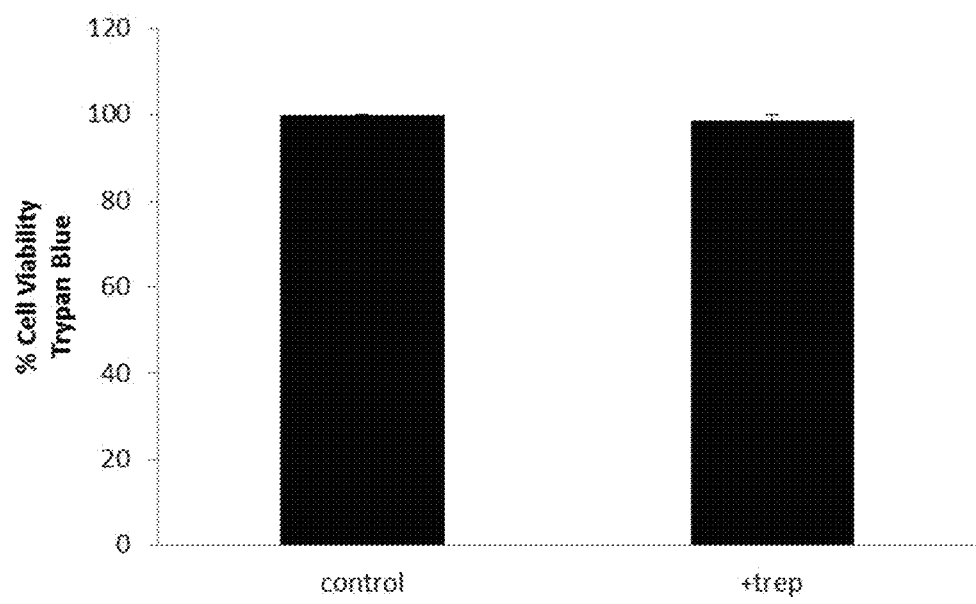

Cells that were exposed to 250 μg/mL of treprostinil for 24 hours (FIG. 7A, right panel) showed no obvious changes in morphology compared to untreated cells (FIG. 7A, left panel). Cell viability was assessed in trypsinized cells in both treprostinil-treated and -untreated cultures. No significant cell death was observed as a result of treprostinil exposure, see FIG. 7B (>95% viability in all replicates and conditions).

Figure 8:
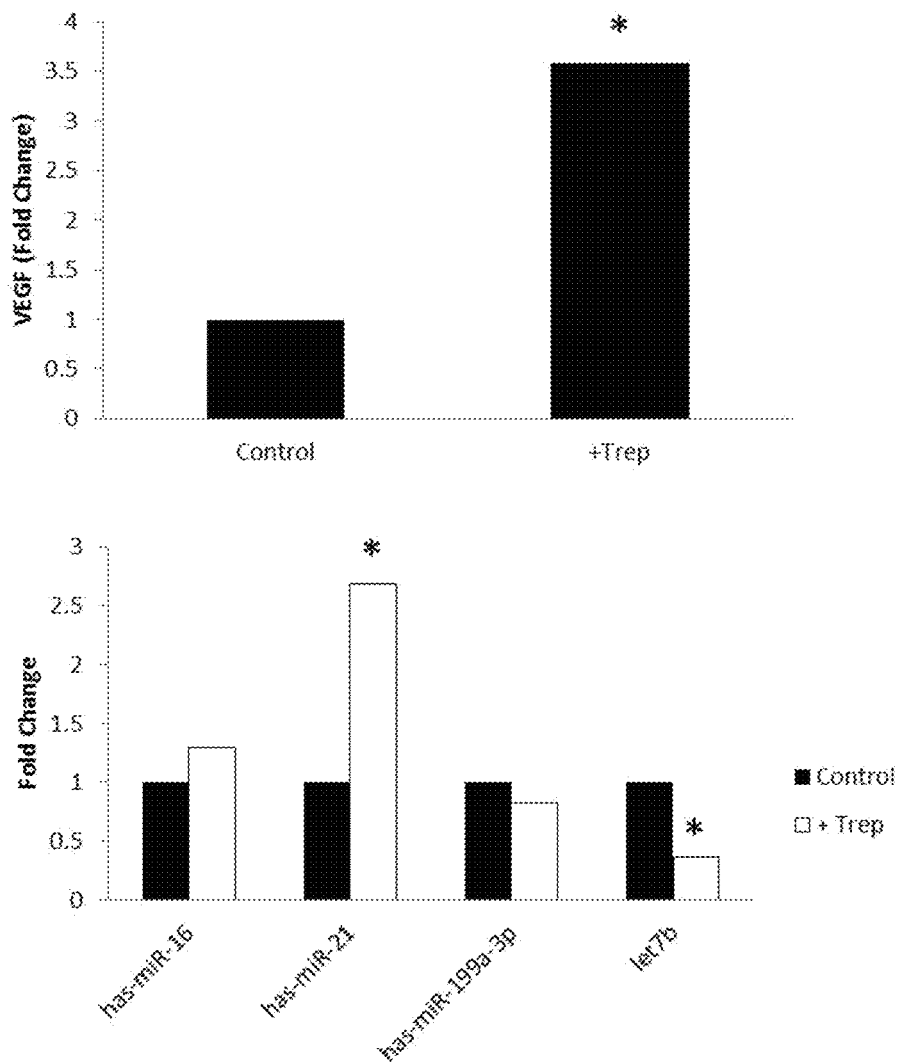
FIG. 8 presents two charts showing altered expression in selected genes in MSC treated with treprostinil.

Gene expression of VEGF-A was confirmed in MSC by qRT-PCR. Treprostinil increased VEGF-A expression ~3.5-fold over untreated controls (FIG. 8, upper panel). Additionally, miR-21 was more abundant in exosomes derived from treprostinil-exposed MSC, while let-7b was less prevalent compared to controls (FIG. 8, lower panel; asterisks indicate statistical significance ($p<0.05$)).

Microarray gene expression analysis was also performed on MSC from cultures without (−) or with (+) 250 ug/mL treprostinil. Three (3) biological replicates from each condition were analyzed. Of the 77,612 sequences identified among all replicates, only 24,273 were detected above the arbitrary background of 50 counts. 2,984 RNA sequences were unique to Tre(−) cultures, while 1,781 RNA sequences were unique to Tre(+) cultures (panel A). Genes detected in both conditions were further analyzed for differential expression (panel). Of the 19,508 genes commonly expressed, only 1,690 differed significantly ($p<0.01$). 268 genes were found to be at least 4-fold higher in untreated MSC, and 171 were found to be at least 4-fold higher in Tre(+) MSC cultures.

Figure 9A:
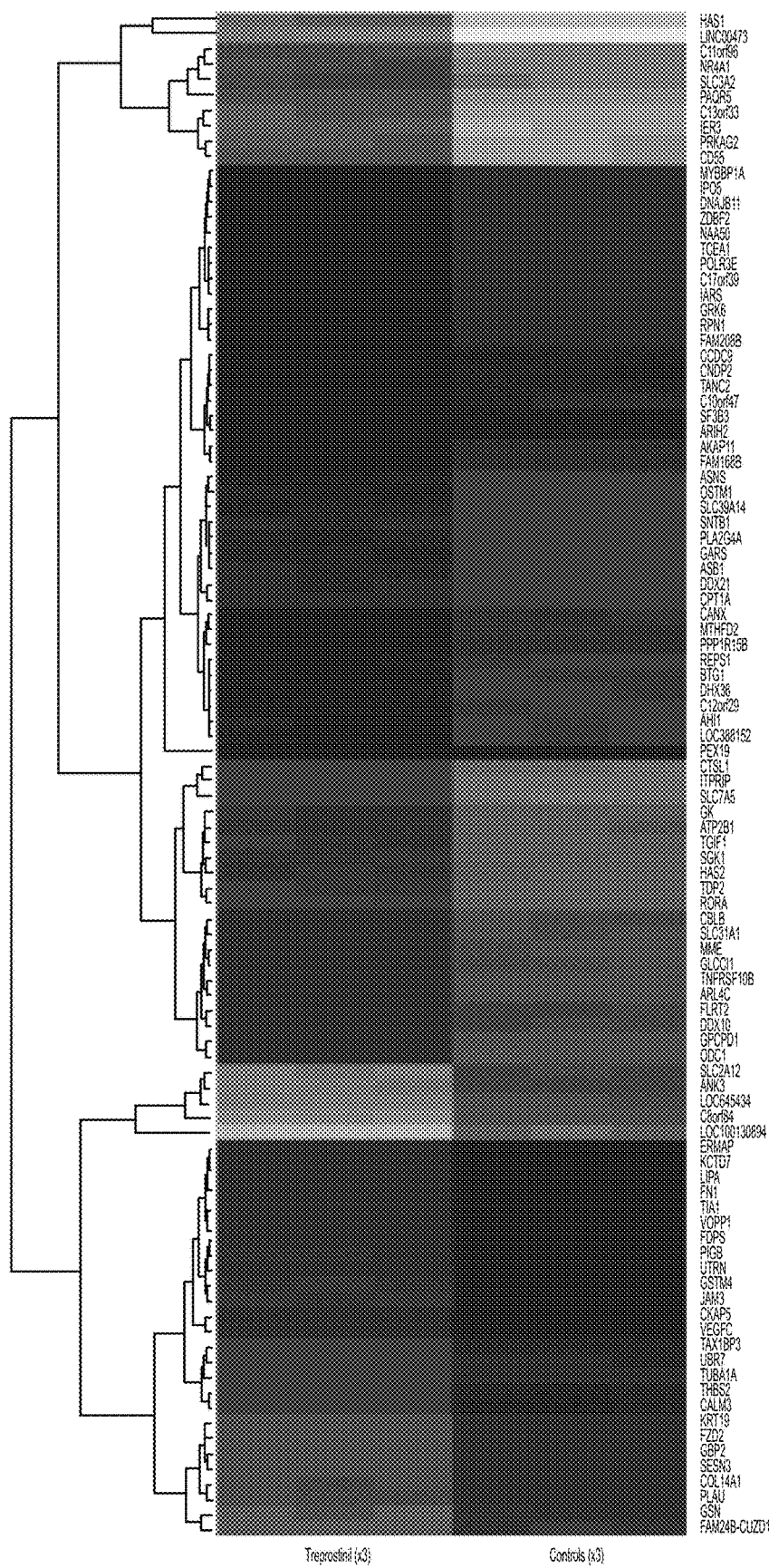
FIG. 9A-9B present two heatmaps that cluster MSC treated with treprostinil from controls with most significantly differentially expressed genes (FIG. 9A) or other genomic sequences or expression tags (FIG. 9B).
Figure 9B:
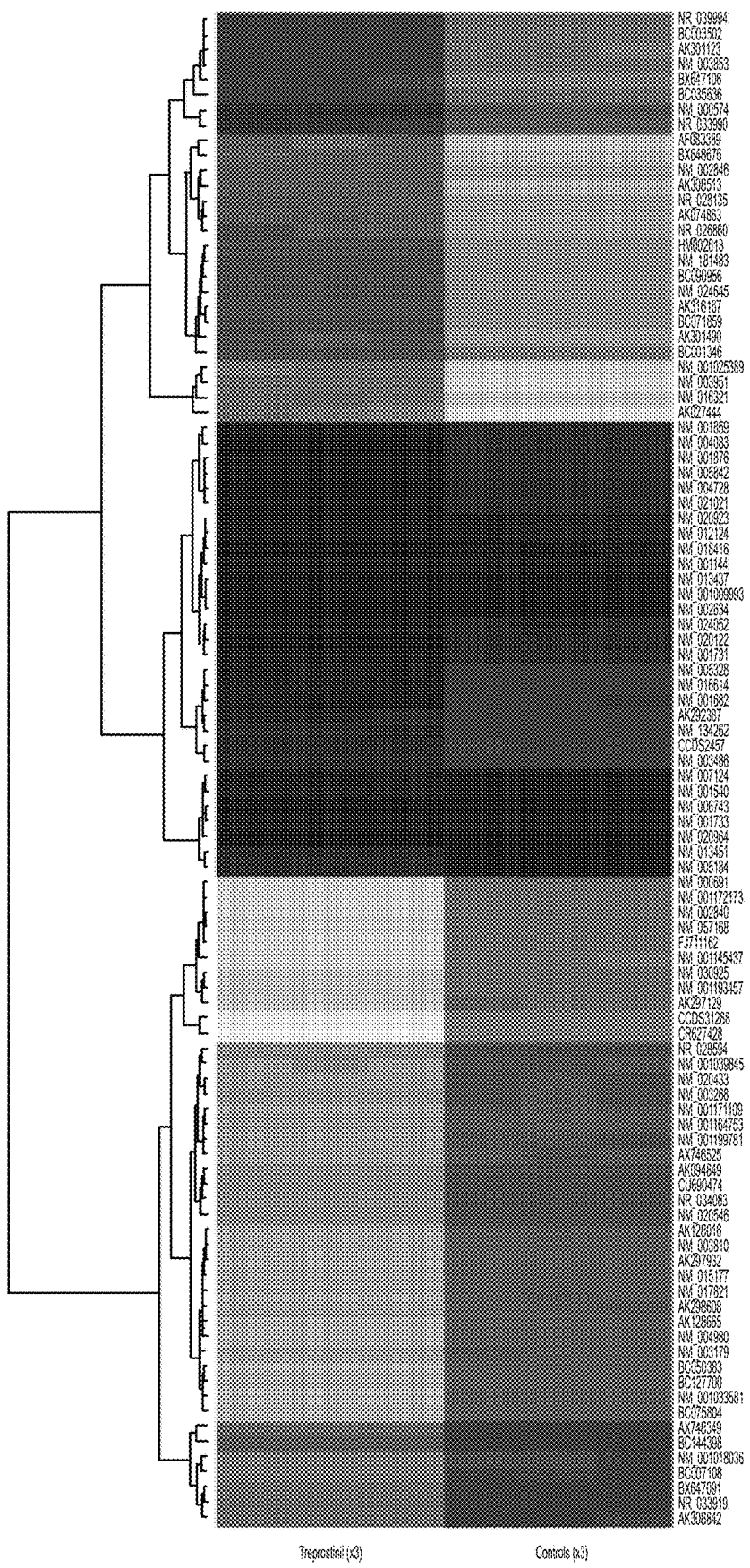

As shown in FIGS. 9A and 9B, differentially expressed genes clearly separated (in terms of clustering) Tre(+) MSC cultures from controls, suggesting that treprostinil exhibited significant impact on the function or activity of the MSC cells.

Tables 2-3 list genes that are upregulated in response to treprostinil. Genes that are expressed only in Tre(+) cultures with at least an average value of 500 counts are shown in Table 2. Genes that are expressed at least 10-fold higher in Tre(+) compared to untreated cells are shown in Table 3.

Tables 4-5 list genes that are downregulated in response to treprostinil. Genes that are downregulated at least 10-fold in Tre(+) cultures are shown in Table 4. Genes that are expressed only in Tre(−) cultures (that is to say, completely turned off in the Tre(+) cultures) are shown in Table 5.

TABLE 2

Gene expressed in Tre(+) only with >500 counts

| Gene | Refseq | Description | Treprostinil (−) | | | | Treprostinil (+) | | | | Fold Change |
|---|---|---|---|---|---|---|---|---|---|---|---|
| | | | Rep 1 | Rep 2 | Rep 3 | AVG | Rep 1 | Rep 2 | Rep 3 | AVG | |
| PTGS2 | NM_000963 | Prostaglandin-endoperoxide synthase 2 (prostaglandin G/H synthase and cyclooxygenase) | 0 | 81 | 56 | 46 | 10216 | 1467 3 | 7776 | 10888 | N/A |
| ANGPTL4 | NM_139314 | Angiopoietin-like 4, transcript variant 1 | 0 | 8 | 5 | 4 | 1570 | 2337 | 1371 | 1759 | N/A |
| HAS1 | NM_001523 | Hyaluronan synthase 1 | 0 | 0 | 69 | 23 | 1149 | 2571 | 1465 | 1728 | N/A |
| PDE4D | NM_001197222 | Phosphodiesterase 4D, cAMP-specific, transcript variant 8 | 49 | 0 | 0 | 16 | 1417 | 2044 | 1570 | 1677 | N/A |
| STC1 | NM_003155 | Stanniocalcin 1 | 29 | 54 | 26 | 36 | 1313 | 2344 | 1095 | 1584 | N/A |
| PDK4 | NM_002612 | Pyruvate dehydrogenase kinase, isozyme 4, nuclear gene encoding mitochondrial protein | 27 | 47 | 26 | 33 | 1296 | 1726 | 1173 | 1399 | N/A |
| NGFR | NM_002507 | Nerve growth factor receptor | 18 | 10 | 19 | 16 | 1217 | 1818 | 1074 | 1370 | N/A |
| BMP6 | NM_001718 | Bone morphogenetic protein 6 | 37 | 43 | 37 | 39 | 1210 | 1581 | 1181 | 1324 | N/A |
| PLOD2 | NM_000935 | Procollagen-lysine, 2-oxoglutarate 5-dioxygenase 2, transcript variant 2 | 68 | 29 | 27 | 42 | 1169 | 1679 | 925 | 1258 | N/A |
| ATF3 | NM_001030287 | Activating transcription factor 3, transcript variant 3 | 0 | 46 | 31 | 26 | 1001 | 1579 | 1041 | 1207 | N/A |
| PDE4B | NM_001037339 | Phosphodiesterase 4B, cAMP-specific, transcript variant b | 0 | 36 | 7 | 14 | 1160 | 1371 | 1056 | 1196 | N/A |
| PDE4D | NM_001197221 | Phosphodiesterase 4D, cAMP-specific, transcript variant 7 | 0 | 74 | 33 | 36 | 1130 | 1170 | 1071 | 1124 | N/A |
| SLC16A6 | NM_004694 | Solute carrier family 16, member 6 (monocarboxylic acid transporter 7), transcript variant 2 | 7 | 11 | 11 | 10 | 975 | 1342 | 784 | 1034 | N/A |

TABLE 2-continued

Gene expressed in Tre(+) only with >500 counts

| Gene | Refseq | Description | Treprostinil (−) | | | | Treprostinil (+) | | | | Fold Change |
|---|---|---|---|---|---|---|---|---|---|---|---|
| | | | Rep 1 | Rep 2 | Rep 3 | AVG | Rep 1 | Rep 2 | Rep 3 | AVG | |
| HAS1 | NM_001523 | Hyaluronan synthase 1 | 0 | 0 | 0 | 0 | 1355 | 730 | 789 | 958 | N/A |
| SMOX | NM_175840 | Spermine oxidase, transcript variant 2 | 65 | 0 | 3 | 77 | 835 | 1372 | 658 | 955 | N/A |
| IL11 | NM_000641 | Interleukin 11 | 18 | 66 | 65 | 50 | 851 | 1237 | 700 | 929 | N/A |
| KYNU | NM_003937 | Kynureninase, transcript variant 1 | 33 | 33 | 16 | 27 | 867 | 922 | 797 | 862 | N/A |
| GDNF | NM_000514 | Glial cell derived neurotrophic factor, transcript variant 1 | 64 | 65 | 0 | 43 | 689 | 845 | 824 | 786 | N/A |
| GDNF | NM_199231 | Glial cell derived neurotrophic factor, transcript variant 2 | 0 | 0 | 0 | 0 | 775 | 1013 | 464 | 751 | N/A |
| SEC31A | NM_001077207 | SEC31 homolog A (S. cerevisiae), transcript variant 5 | 121 | 0 | 0 | 40 | 737 | 887 | 573 | 732 | N/A |
| PAQR5 | NM_017705 | Progestin and adipoQ receptor family member V, transcript variant 2 | 35 | 60 | 48 | 48 | 703 | 745 | 664 | 704 | N/A |
| ATF3 | NM_001674 | Activating transcription factor 3, transcript variant 1 | 48 | 24 | 40 | 37 | 668 | 920 | 442 | 676 | N/A |
| ATP6V0D2 | NM_152565 | ATPase, H+ transporting, lysosomal 38 kDa, V0 subunit d2 | 9 | 15 | 6 | 10 | 547 | 893 | 499 | 646 | N/A |
| KTN1 | NM_001079522 | Kinectin 1 (kinesin receptor), transcript variant 3 | 47 | 0 | 73 | 40 | 531 | 612 | 596 | 579 | N/A |
| SLC4A2 | NM_001199693 | Solute carrier family 4, anion exchanger, member 2, transcript variant 3 | 47 | 0 | 0 | 16 | 821 | 176 | 574 | 524 | N/A |
| TRH | NM_007117 | Thyrotropin-releasing hormone (TRH), mRNA. | 12 | 13 | 7 | 11 | 419 | 697 | 428 | 515 | N/A |
| ST6GALNAC6 | NM_013443 | ST6 galactosyl-N-acetylgalactosaminide-sialyltransferase 6 | 7 | 0 | 0 | 2 | 424 | 651 | 445 | 506 | N/A |

TABLE 3

Genes with 10-fold increase om Tre(+) compared to Tre(−)

| Gene | Refseq | Description | Treprostinil (−) | | | | Treprostinil (+) | | | | Fold Change |
|---|---|---|---|---|---|---|---|---|---|---|---|
| | | | Rep 1 | Rep 2 | Rep 3 | AVG | Rep 1 | Rep 2 | Rep 3 | AVG | |
| IGFBP1 | NM_000596 | Insulin-like growth factor binding protein 1 | 40 | 78 | 42 | 53 | 5468 | 8123 | 5321 | 6304 | 118.2 |
| IL6 | NM_000600 | Interleukin 6 (interferon, beta 2) | 49 | 86 | 53 | 63 | 6490 | 8445 | 5640 | 6859 | 109.5 |
| PRKAG2 | NM_024429 | Protein kinase, AMP-activated, gamma 2 non-catalytic subunit, transcript variant b | 75 | 112 | 85 | 91 | 7233 | 8152 | 6080 | 7155 | 78.6 |
| PLIN2 | NM_001122 | Perilipin 2, transcript variant 1 | 1608 | 2409 | 1910 | 1976 | 82301 | 124225 | 72254 | 92927 | 47.0 |
| GDF15 | NM_004864 | Growth differentiation factor 15 | 321 | 583 | 358 | 421 | 11450 | 18978 | 10088 | 13505 | 32.1 |
| SLC6A15 | NM_182767 | Solute carrier family 6 (neutral amino acid transporter), member 15, transcript variant 1 | 36 | 89 | 36 | 54 | 1201 | 1568 | 1062 | 1277 | 23.7 |
| IER3 | NM_003897 | Immediate early response 3 | 108 | 152 | 136 | 132 | 2769 | 3595 | 2558 | 2974 | 22.5 |
| CD55 | NM_000574 | CD55 molecule, decay accelerating factor for complement, transcript variant 1 | 258 | 452 | 367 | 359 | 7472 | 9108 | 6555 | 7712 | 21.5 |
| SCG2 | NM_003469 | Secretogranin II | 49 | 56 | 49 | 51 | 1014 | 1187 | 1069 | 1090 | 21.3 |
| C13orf33 | NM_032849 | Chromosome 13 open reading frame 33 | 737 | 1129 | 889 | 918 | 17304 | 24329 | 16255 | 19296 | 21.0 |
| SIK1 | NM_173354 | Salt-inducible kinase 1 | 34 | 79 | 62 | 58 | 1144 | 1320 | 1086 | 1183 | 20.3 |
| PITPNC1 | NM_181671 | Phosphatidylinositol transfer protein, cytoplasmic 1, transcript variant 2 | 33 | 65 | 57 | 52 | 702 | 1007 | 764 | 824 | 16.0 |
| HSD11B1 | NM_005525 | Hydroxysteroid (11-beta) dehydrogenase 1, transcript variant 1 | 54 | 87 | 24 | 55 | 822 | 966 | 758 | 849 | 15.4 |
| SAT1 | | Spermidine/spermine N1-acetyltransferase 1, transcript variant 2, non-coding RNA | 68 | 138 | 62 | 89 | 1141 | 1529 | 954 | 1208 | 13.5 |
| VEGFA | NM_001025370 | Vascular endothelial growth factor A, transcript variant 6 | 389 | 510 | 260 | 386 | 4761 | 6614 | 4293 | 5223 | 13.5 |
| PALLD | NM_001166110 | Palladin, cytoskeletal associated protein, transcript variant 4 | 0 | 126 | 108 | 78 | 1158 | 885 | 1055 | 1033 | 13.3 |
| GPRC5A | NM_003979 | G protein-coupled receptor, family C, group 5, member A | 279 | 415 | 370 | 355 | 4151 | 5981 | 3920 | 4684 | 13.2 |
| CD55 | NM_001114752 | CD55 molecule, decay accelerating factor for complement, transcript variant 2 | 161 | 214 | 230 | 202 | 2497 | 3119 | 2372 | 2663 | 13.2 |
| LIPG | NM_006033 | Lipase, endothelial | 95 | 171 | 121 | 129 | 1552 | 1946 | 1607 | 1702 | 13.2 |
| IDH1 | NM_005896 | Isocitrate dehydrogenase 1 (NADP+), soluble | 129 | 223 | 114 | 155 | 1920 | 2406 | 1792 | 2039 | 13.1 |

TABLE 3-continued

Genes with 10-fold increase om Tre(+) compared to Tre(−)

| Gene | Refseq | Description | Treprostinil (−) | | | | Treprostinil (+) | | | | Fold Change |
|---|---|---|---|---|---|---|---|---|---|---|---|
| | | | Rep 1 | Rep 2 | Rep 3 | AVG | Rep 1 | Rep 2 | Rep 3 | AVG | |
| RND3 | NM_005168 | Rho family GTPase 3, transcript variant 2 | 3542 | 4708 | 3790 | 4013 | 48372 | 65016 | 41881 | 51756 | 12.9 |
| DUSP1 | NM_004417 | Dual specificity phosphatase 1 | 66 | 98 | 91 | 85 | 825 | 1489 | 963 | 1092 | 12.9 |
| NR4A2 | NM_006186 | Nuclear receptor subfamily 4, group A, member 2 | 39 | 66 | 59 | 55 | 635 | 810 | 592 | 679 | 12.5 |
| C11orf96 | NM_001145033 | Chromosome 11 open reading frame 96 | 148 | 203 | 177 | 176 | 2050 | 2381 | 1885 | 2105 | 12.0 |
| PTP4A1 | NM_003463 | Protein tyrosine phosphatase type IVA, member 1 | 0 | 174 | 0 | 58 | 849 | 696 | 510 | 685 | 11.8 |
| SREBF1 | NM_004176 | Sterol regulatory element binding transcription factor 1, transcript variant 2 | 0 | 1 | 444 | 148 | 1709 | 1842 | 1577 | 1709 | 11.5 |
| VEGFA | NM_001171626 | Vascular endothelial growth factor A, transcript variant 4 | 470 | 756 | 765 | 664 | 6586 | 9874 | 6349 | 7603 | 11.5 |
| RCAN1 | NM_203418 | Regulator of calcineurin 1, transcript variant 3 | 511 | 863 | 1068 | 814 | 7766 | 11997 | 6962 | 8908 | 10.9 |
| SLC3A2 | NM_001013251 | Solute carrier family 3, member 2, transcript variant 6 | 2478 | 4147 | 2946 | 3190 | 31831 | 39703 | 29042 | 33526 | 10.5 |

TABLE 4

Genes with 10-fold decrease in Tre(+) compared to Tre(−)

| Gene | Refseq | Description | Treprostinil (−) | | | | Treprostinil (+) | | | | Fold Change |
|---|---|---|---|---|---|---|---|---|---|---|---|
| | | | Rep 1 | Rep 2 | Rep 3 | AVG | Rep 1 | Rep 2 | Rep 3 | AVG | |
| ISLR | NM_005545 | Immunoglobulin superfamily containing leucine-rich repeat, transcript variant 1 | 4070 | 7084 | 5446 | 5533 | 612 | 543 | 490 | 548 | 10.1 |
| S100A4 | NM_002961 | S100 calcium binding protein A4, transcript variant 1 | 1057 | 1585 | 1294 | 1312 | 149 | 114 | 113 | 125 | 10.5 |
| CELF1 | NM_001172640 | CUGBP, Elav-like family member 1, transcript variant 5 | 648 | 628 | 658 | 644 | 80 | 66 | 31 | 59 | 10.9 |
| EPB41L2 | NM_001199389 | Erythrocyte membrane protein band 4.1-like 2 (EPB41L2), transcript variant 5 | 935 | 1631 | 1251 | 1272 | 146 | 63 | 131 | 113 | 11.2 |
| RCAN2 | NM_001251974 | Regulator of calcineurin 2, transcript variant 2 | 989 | 1346 | 1318 | 1218 | 129 | 109 | 76 | 105 | 11.6 |
| ANLN | NM_018685 | Anillin, actin binding protein | 595 | 885 | 528 | 669 | 67 | 68 | 37 | 57 | 11.7 |
| COL6A3 | NM_004369 | Collagen, type VI, alpha 3, transcript variant 1 | 41492 | 68881 | 52605 | 54326 | 5033 | 4570 | 4303 | 4635 | 11.7 |
| MEST | NM_177525 | Mesoderm specific transcript homolog (mouse), transcript variant 3 | 2666 | 4031 | 3958 | 3552 | 367 | 268 | 258 | 298 | 11.9 |
| METTL7A | NM_014033 | Methyltransferase like 7A | 1075 | 1603 | 1220 | 1299 | 146 | 95 | 85 | 109 | 11.9 |
| CPA4 | NM_016352 | Carboxypeptidase A4, transcript variant 1 | 461 | 740 | 693 | 631 | 51 | 62 | 45 | 53 | 12.0 |
| SLC2A12 | NM_145176 | Solute carrier family 2 (facilitated glucose transporter), member 12 | 1049 | 1525 | 1269 | 1281 | 110 | 114 | 92 | 105 | 12.2 |
| OLFML1 | NM_198474 | Olfactomedin-like 1 | 1204 | 2191 | 1808 | 1734 | 177 | 128 | 114 | 140 | 12.4 |
| GDF5 | NM_000557 | Growth differentiation factor 5 | 721 | 1190 | 739 | 883 | 83 | 64 | 65 | 71 | 12.5 |
| DDAH1 | NM_001134445 | Dimethylarginine dimethylaminohydrolase 1, transcript variant 2 | 1369 | 2058 | 1626 | 1685 | 136 | 155 | 107 | 133 | 12.7 |
| ACTN1 | NM_001130005 | Actinin, alpha 1, transcript variant 3 | 1104 | 1891 | 1381 | 1459 | 165 | 115 | 64 | 115 | 12.7 |
| PRELP | NM_002725 | Proline/arginine-rich end leucine-rich repeat protein, transcript variant 1 | 1166 | 1673 | 1582 | 1474 | 159 | 104 | 80 | 114 | 12.9 |
| PALLD | NM_001166109 | Palladin, cytoskeletal associated protein, transcript variant 3 | 7556 | 11050 | 10821 | 9809 | 1116 | 638 | 503 | 753 | 13.0 |
| DKFZp547J0510 | | CDNA FLJ42650 fis, clone BRACE3027478 | 1345 | 2491 | 1958 | 1932 | 183 | 135 | 125 | 148 | 13.0 |
| ANK3 | NM_001204403 | Ankyrin 3, node of Ranvier (ankyrin G), transcript variant 3 | 573 | 1098 | 762 | 811 | 86 | 59 | 27 | 57 | 14.2 |
| ANGPT1 | NM_001146 | Angiopoietin 1, transcript variant 1 | 518 | 1017 | 804 | 780 | 80 | 73 | 7 | 53 | 14.6 |
| MEST | NM_002402 | Mesoderm specific transcript homolog (mouse), transcript variant 1 | 866 | 1719 | 1264 | 1283 | 98 | 138 | 20 | 85 | 15.1 |
| PDE5A | NM_033430 | Phosphodiesterase 5A, cGMP-specific, transcript variant 2 | 2547 | 3986 | 3551 | 3361 | 174 | 286 | 206 | 222 | 15.2 |
| CXCL12 | NM_199168 | Chemokine (C—X—C motif) ligand 12, transcript variant 1 | 8468 | 12501 | 10752 | 10574 | 853 | 627 | 534 | 671 | 15.8 |
| SLC14A1 | NM_015865 | Solute carrier family 14 (urea transporter), member 1, transcript variant 2 | 1328 | 2174 | 1360 | 1621 | 95 | 102 | 67 | 88 | 18.5 |

TABLE 4-continued

Genes with 10-fold decrease in Tre(+) compared to Tre(-)

| Gene | Refseq | Description | Treprostinil (−) Rep 1 | Rep 2 | Rep 3 | AVG | Treprostinil (+) Rep 1 | Rep 2 | Rep 3 | AVG | Fold Change |
|---|---|---|---|---|---|---|---|---|---|---|---|
| OLFML2B | NM_015441 | Olfactomedin-like 2B | 1147 | 1802 | 1447 | 1465 | 115 | 60 | 36 | 70 | 20.8 |
| SYNPO2 | NM_001128933 | Synaptopodin 2, transcript variant 2 | 1812 | 2822 | 3020 | 2551 | 142 | 104 | 65 | 104 | 24.6 |
| LMOD1 | NM_012134 | Leiomodin 1 (smooth muscle) | 1235 | 1960 | 1972 | 1722 | 107 | 51 | 38 | 65 | 26.4 |
| COL21A1 | NM_030820 | Collagen, type XXI, alpha 1 | 1125 | 1991 | 1590 | 1569 | 78 | 57 | 37 | 57 | 27.4 |
| CTGF | NM_001901 | Connective tissue growth factor | 16535 | 26281 | 26219 | 23012 | 1125 | 603 | 494 | 741 | 31.1 |
| MXRA5 | NM_015419 | Matrix-remodelling associated 5 | 1333 | 2083 | 1861 | 1759 | 97 | 28 | 37 | 54 | 32.6 |

TABLE 5

Gene expressed in Tre(−) only with >500 counts

| Gene | Refseq | Description | Treprostinil (−) Rep 1 | Rep 2 | Rep 3 | AVG | Treprostinil (+) Rep 1 | Rep 2 | Rep 3 | AVG | Fold Change |
|---|---|---|---|---|---|---|---|---|---|---|---|
| TIAM2 | NM_012454 | T-cell lymphoma invasion and metastasis 2, transcript variant 1 | 326 | 593 | 592 | 504 | 0 | 24 | 31 | 20 | N/A |
| KIAA0930 | NM_015264 | KIAA0930, transcript variant 1 | 504 | 577 | 453 | 511 | 99 | 9 | 36 | 48 | N/A |
| CALD1 | NM_033140 | Caldesmon 1, transcript variant 5 | 605 | 370 | 594 | 523 | 0 | 0 | 0 | 0 | N/A |
| MBNL1 | NM_207297 | Muscleblind-like (Drosophila), transcript variant 7 | 293 | 719 | 565 | 526 | 138 | 0 | 0 | 46 | N/A |
| NAP1L3 | NM_004538 | Nucleosome assembly protein 1-like 3 | 449 | 655 | 510 | 538 | 68 | 35 | 42 | 48 | N/A |
| CLDN11 | NM_005602 | Claudin 11, transcript variant 1 | 446 | 786 | 398 | 543 | 2 | 38 | 0 | 13 | N/A |
| FAM198B | NM_001128424 | Family with sequence similarity 198, member B, transcript variant 3 | 543 | 811 | 323 | 559 | 0 | 0 | 46 | 15 | N/A |
| SLC7A8 | NM_182728 | Solute carrier family 7, member 8, transcript variant 2 | 427 | 815 | 598 | 613 | 91 | 0 | 39 | 43 | N/A |
| ASPM | NM_018136 | Asp (abnormal spindle) homolog, microcephaly associated (Drosophila), transcript variant 1 | 538 | 826 | 510 | 625 | 20 | 27 | 30 | 26 | N/A |
| TCF12 | NM_207040 | Transcription factor 12, transcript variant 5 | 593 | 803 | 549 | 648 | 0 | 119 | 0 | 40 | N/A |
| SCN2A | NM_021007 | Sodium channel, voltage-gated, type II, alpha subunit, transcript variant 1 | 488 | 848 | 621 | 652 | 0 | 23 | 38 | 20 | N/A |
| ASPH | NM_001164754 | Aspartate beta-hydroxylase, transcript variant 10 | 591 | 1048 | 335 | 658 | 111 | 0 | 0 | 37 | N/A |
| CIT | NM_001206999 | Citron (rho-interacting, serine/threonine kinase 21), transcript variant 1 | 548 | 862 | 575 | 661 | 0 | 27 | 0 | 9 | N/A |
| TPM1 | NM_001018007 | Tropomyosin 1 (alpha), transcript variant 2 | 816 | 267 | 1109 | 731 | 107 | 0 | 0 | 36 | N/A |
| ST8SIA1 | NM_003034 | ST8 alpha-N-acetyl-neuraminide alpha-2,8-sialyltransferase 1 | 590 | 912 | 691 | 731 | 81 | 0 | 54 | 45 | N/A |
| FAM84A | NM_145175 | Family with sequence similarity 84, A | 564 | 923 | 712 | 733 | 63 | 40 | 32 | 45 | N/A |
| SPATA20 | NM_022827 | Spermatogenesis associated 20 | 707 | 925 | 568 | 733 | 45 | 0 | 0 | 15 | N/A |
| PRRT2 | NM_145239 | Proline-rich transmembrane protein 2, transcript variant 1 | 587 | 955 | 691 | 744 | 65 | 19 | 24 | 36 | N/A |
| LRRC17 | NM_001031692 | Leucine rich repeat containing 17, transcript variant 1 | 608 | 896 | 733 | 746 | 43 | 11 | 13 | 22 | N/A |
| SNX14 | NM_153816 | Sorting nexin 14, transcript variant 1 | 602 | 1135 | 702 | 813 | 55 | 0 | 0 | 18 | N/A |
| OLFML1 | NM_198474 | Olfactomedin-like 1 | 742 | 900 | 806 | 816 | 54 | 16 | 56 | 42 | N/A |
| RASA4 | NM_006989 | RAS p21 protein activator 4, transcript variant 1 | 459 | 1209 | 902 | 857 | 34 | 0 | 0 | 11 | N/A |
| MAP1B | NM_005909 | Microtubule-associated protein 1B | 556 | 915 | 1188 | 886 | 47 | 0 | 80 | 42 | N/A |
| MEOX2 | NM_005924 | Mesenchyme homeobox 2 | 727 | 1124 | 1093 | 982 | 57 | 10 | 25 | 31 | N/A |
| MYLK | NM_053025 | Myosin light chain kinase, transcript variant 1 | 602 | 1519 | 852 | 991 | 0 | 0 | 0 | 0 | N/A |
| SLC14A1 | NM_015865 | Solute carrier family 14 (urea transporter), member 1, transcript variant 2 | 732 | 1312 | 1065 | 1036 | 38 | 13 | 7 | 19 | N/A |
| FLG | NM_002016 | Filaggrin | 751 | 1239 | 1165 | 1052 | 45 | 17 | 22 | 28 | N/A |
| ARPC4 | NM_001024960 | Actin related protein 2/3 complex, subunit 4, 20 kDa, transcript variant 3 | 1236 | 924 | 1289 | 1150 | 35 | 0 | 0 | 12 | N/A |
| RBFOX2 | NM_001031695 | RNA binding protein, fox-1 homolog (*C. elegans*) 2, transcript variant 1 | 1529 | 1132 | 1289 | 1316 | 26 | 4 | 0 | 10 | N/A |
| ASPH | NM_004318 | Aspartate beta-hydroxylase, transcript variant 1 | 3340 | 3680 | 1137 | 2719 | 3 | 1 | 0 | 1 | N/A |
| SREBF1 | NM_001005291 | Sterol regulatory element binding transcription factor 1, transcript variant 1 | 2304 | 4238 | 2265 | 2936 | 36 | 0 | 0 | 12 | N/A |

Bead-based immunoassays (Luminex) was performed to assess the concentration of 46 cytokines in cell culture supernatants (Myriad RBM Human InflammationMAP® 1.0). Of the 46 evaluated, 6 were differentially secreted in treprostinil-treated and -untreated MSC cultures (see Table 6, n=3 per group). Asterisks indicate statistical significance between the groups based on a Student's T Test (*p<0.001, or **p<0.0001).

TABLE 6

Inflammatory cytokine secretion is altered in MSC treated with treprostinil

| Protein Name | Abbreviation | (+) Treprostinil | (−) Treprostinil |
|---|---|---|---|
| Ferritin | FRTN | 0.96 +/− 0.01 ng/ml (INCREASED) | 0.70 +/− 0.11 ng/mL |
| Interleukin-6 | IL-6 | 3580 +/− 384 pg/mL** (INCREASED) | 62 +/− 6 pg/ml |
| Interleukin-8 | IL-8 | Below detection (DECREASED) | 2.4 +/− 1.0 pg/ml |
| Monocyte Chemotactic Protein 1 | MCP-1 | 47 +/− 9 pg/mL** (DECREASED) | 379 +/− 35 pg/ml |
| Tissue Inhibitor of Metalloproteinases 1 | TIMP-1 | 12 +/− 1 ng/mL* (DECREASED) | 29 +/− 3 ng/ml |
| Vascular Endothelial Growth Factor | VEGF | 612 +/− 37 pg/mL** (INCREASED) | 235 +/− 16 pg/ml |

Figure 10:
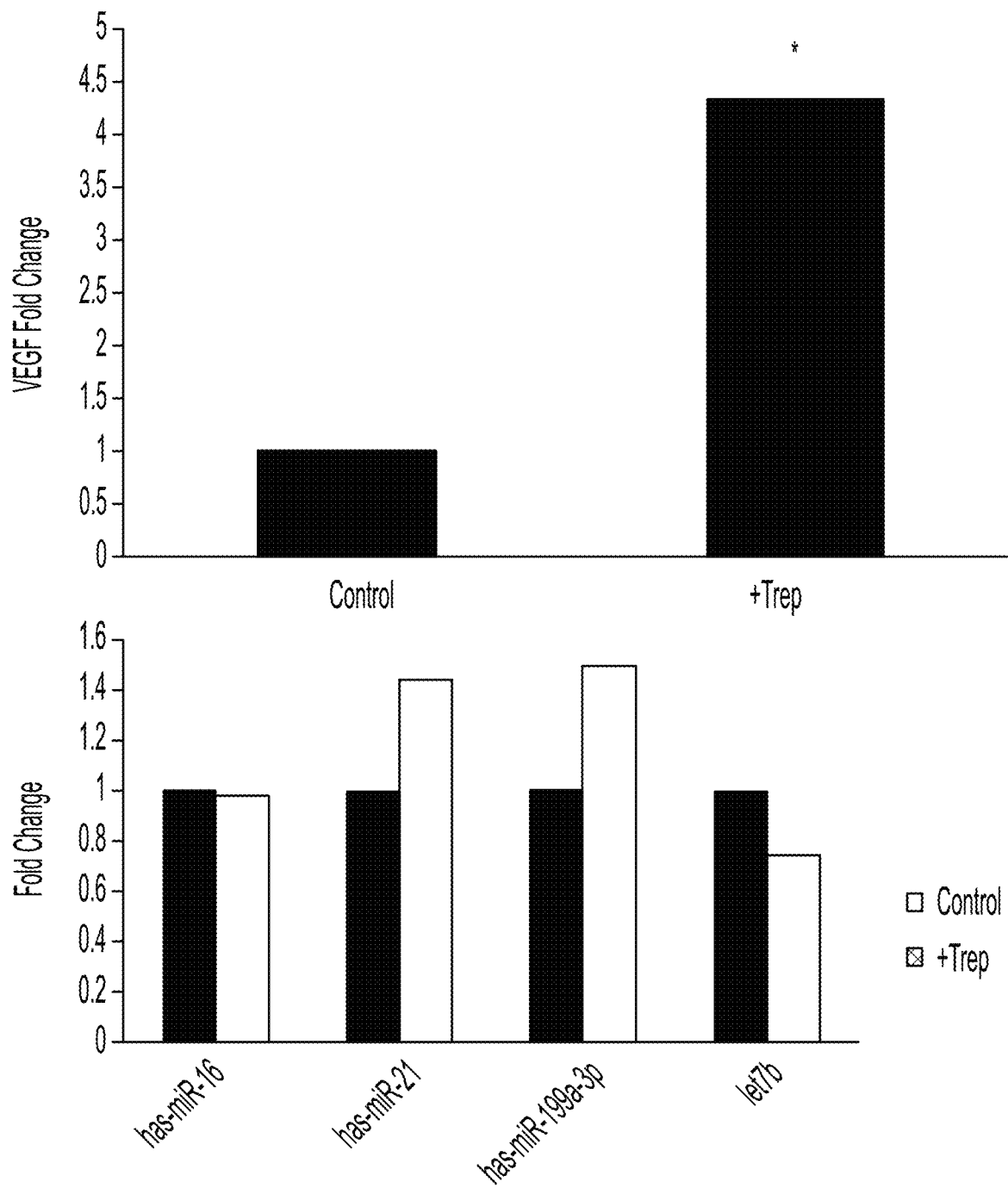
FIG. 10 presents charts showing that the RNA content in MSC-derived exosomes is altered with treprostinil treatment.

Total RNA was extracted from exosomal preparations, and qRT-PCR was performed with the same primer/probe sets used in experiments with the parent cells (refer to FIG. 8). VEGF-A gene transcripts present in MSC-derived exosomes were increased ~4-fold as a result of treprostinil exposure (FIG. 10). Additionally, miR-21 and miR-199-3p were significantly more abundant in exosomes derived from treprostinil-treated cells (p<0.05).

This example shows that the gene expression and secretory profiles of MSC were altered upon 24 hours of exposure to treprostinil in vitro. Treprostinil increased the angiogenic potential of MSC based on the observation that VEGF protein and gene were both increased. Furthermore, the exosomes of treprostinil-treated MSC had higher levels of VEGF-A, which could promote increased VEGF production in target cells through a mechanism of horizontal gene transfer.

Furthermore, miR-21 and miR-199a-3p were observed, which could also influence the activity in target cells (Lee et al., *Circulation* 126(22):2601-11, 2012). Changes in secreted cytokines were also observed as a result of treprostinil exposure. In particular, IL-6 was produced ~50-fold more compared to control MSC, while MCP-1 was secreted ~6-7-fold less.

Example 4. Physical Analysis of Exosomes Derived from MSC Exposed to 250 μg/mL Treprostinil The experimental procedure described in Example 3 was repeated to generate enough exosomes for additional analysis. Conditioned media from treprostinil-treated and -untreated MSC cultures were analyzed by tunable pulse resistive sensing (TRPS). This method quantifies the number of particles suspended in a sample, as well as the size of each particle, based on changes in electrical current through the sample.

Figure 11A:
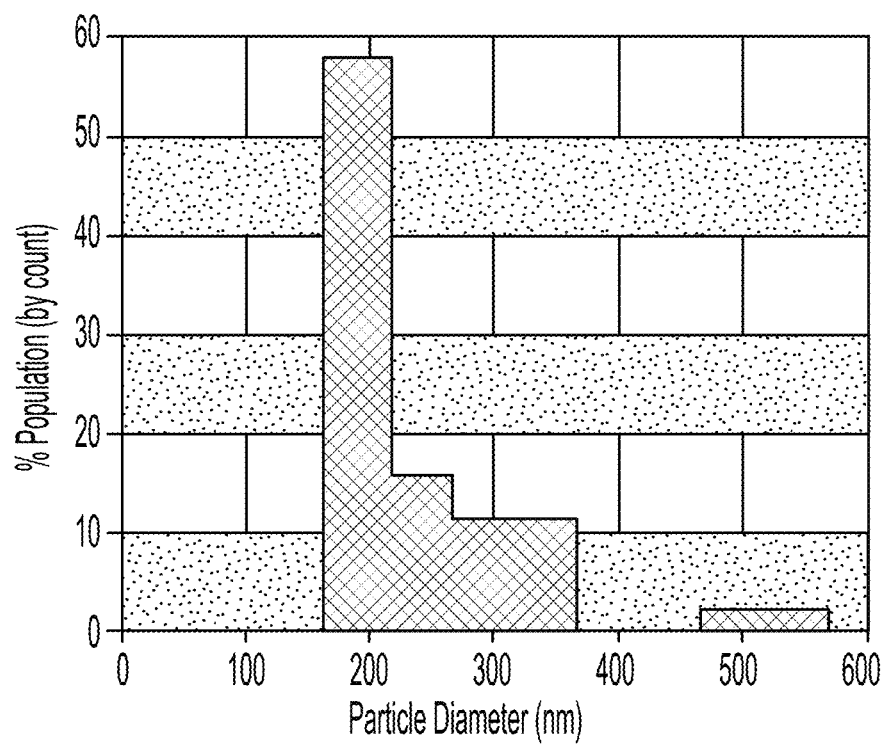
FIG. 11A-11B show size distribution of exosomes derived from treprostinil-treated and -untreated MSC.
Figure 11B:
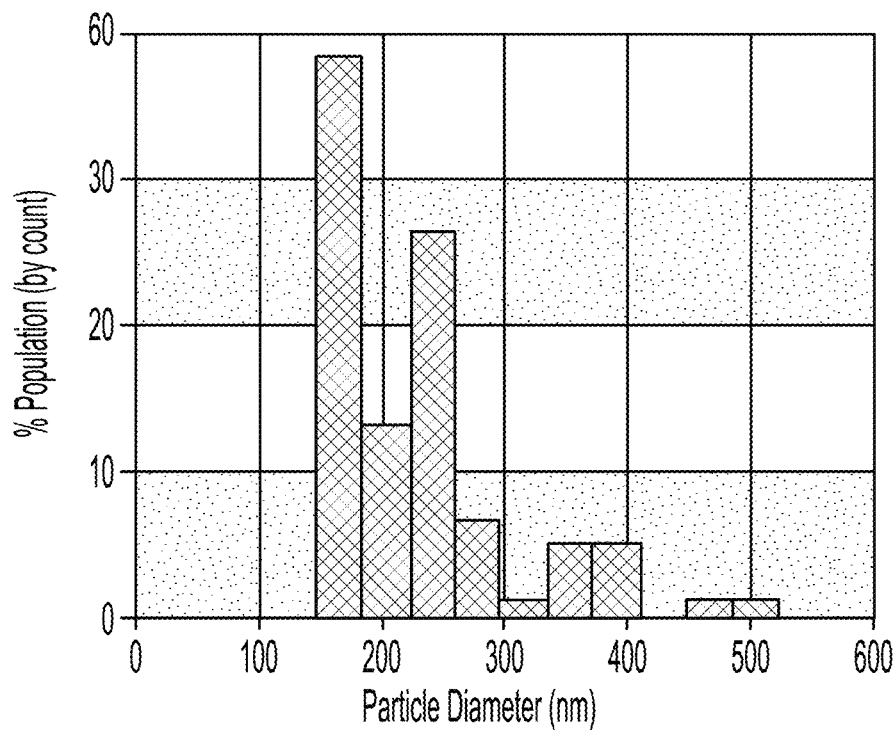

Size distribution of exosomes derived from treprostinil-treated and -untreated MSC is presented in FIG. 11A-B. Exosome preparations from treprostinil-treated MSC (FIG. 11A) and -untreated MSC (FIG. 11B) were analyzed for 50-600 nm sized particles by tunable resistive pulse sensing (TRPS). These representative histograms for each exosome population demonstrated that a majority of the particles were 150-200 nm in size in both groups. Treprostinil-treat MSC yielded a more uniform population of exosomes, with nearly 60% of the population falling into the ~200 nm size category. Total particle count for each condition was >500 counts.

Particle concentration of exosomal preparations was determined by TRPS. Fewer particles were observed in the (+) Treprostinil preparation compared to control (n=1). Mean size, mode size and size range were comparable between the two groups, and included in Table 7.

TABLE 7

Exosome size and concentration in (+) Treprostinil and (−) Treprostinil preparations

| Parameter | (+) Treprostinil | (−) Treprostinil |
|---|---|---|
| Concentration | 8.9 E6 per mL | 1.5 E7 per mL |
| Mean Diameter | 213.3 nm | 210.0 nm |
| Mode Diameter | 164.4 nm | 147.1 nm |
| Max Diameter | 503.0 nm | 482.8 nm |
| Min Diameter | 139.2 nm | 128.3 nm |

This example suggests that treprostinil could yield a more uniform population of exosomes.

Although the foregoing refers to particular preferred embodiments, it will be understood that the present disclosure is not so limited. It will occur to those of ordinary skill in the art that various modifications may be made to the disclosed embodiments and that such modifications are intended to be within the scope of the present disclosure.

All of the publications, patent applications and patents cited in this specification are incorporated herein by reference in their entirety.

The invention claimed is:

1. A method of preparing a pharmaceutical product a mesenchymal stem cell (MSC) or a part of a culture medium that has been in contact with the MSC and contains one or more components of the MSC, comprising contacting a culture comprising an MSC with a prostacyclin and thereafter isolating the MSC or a part of a culture medium that has been in contact with the MSC and contains one or more components of the MSC.

2. The method of claim 1, wherein the component(s) of the MSC is selected from the group consisting of an exosome, a microvesicle, a microRNA, a messenger RNA, a non-coding RNA, a mitochondria, a growth factor, and combinations thereof.

3. The method of claim 1, wherein the pharmaceutical product further comprises an endothelial progenitor cell (EPC).

4. The method of claim 3, wherein the EPC is obtained from a subject who is to be treated with the pharmaceutical product.

5. The method of claim 4, wherein the EPC is transformed with a nucleic acid that increases the expression of biological activity of a protein selected from the group consisting of endothelial nitric oxide synthase (eNOS), heme oxygenase (HMOX1) and prostacyclin synthase (PTGIS).

6. The method of claim 5, wherein the nucleic acid encodes the protein.

7. The method of claim 1, wherein the prostacyclin is selected from the group consisting of epoprostenol, treprostinil, beraprost, ilprost, a $PGI_2$ receptor agonist, and pharmaceutically acceptable salts thereof.

8. The method of claim 7, wherein the prostacyclin is treprostinil or a pharmaceutically acceptable salt or ester thereof.

9. The method of claim 1, wherein the MSC is a mesenchymal precursor cell (MPC).

10. The method of claim 1, wherein the MSC is obtained from bone marrow.

11. The method of claim 1, wherein contacting with the prostacyclin comprises adding the prostacyclin to the MSC culture at a concentration from about 200 µg/mL to about 300 µg/mL.

12. The method of claim 1, wherein the contacting with the prostacyclin occurs for at least 24 hours.

13. The method of claim 11, wherein the contacting with the prostacyclin occurs for at least 24 hours.

14. The method of claim 13, wherein the prostacyclin is treprostinil.

\* \* \* \* \*